US008483810B2

(12) United States Patent
Lee et al.

(10) Patent No.: US 8,483,810 B2
(45) Date of Patent: Jul. 9, 2013

(54) APPARATUS AND METHOD FOR MONITORING FETUS IN MATERNAL BODY

(75) Inventors: Shiow-Harn Lee, Hsinchu (TW); Chien-Nan Lee, Taipei (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 659 days.

(21) Appl. No.: 12/649,331

(22) Filed: Dec. 30, 2009

(65) Prior Publication Data

US 2011/0092837 A1    Apr. 21, 2011

(30) Foreign Application Priority Data

Oct. 21, 2009   (TW) .............................. 98135638 A

(51) Int. Cl.
*A61B 5/02* (2006.01)
*A61B 5/04* (2006.01)
*A61N 1/39* (2006.01)
*A61N 1/00* (2006.01)

(52) U.S. Cl.
USPC .............. 600/511; 607/1; 607/2; 607/902; 600/508; 600/509; 600/523; 600/483

(58) Field of Classification Search
USPC ............. 600/483, 508, 509, 511, 523; 607/1, 607/2, 902
See application file for complete search history.

(56) References Cited

U.S. PATENT DOCUMENTS

| 4,945,917 A | 8/1990 | Akselrod et al. |
| 5,666,959 A | 9/1997 | Deans et al. |
| 5,957,855 A * | 9/1999 | Oriol et al. ............... 600/511 |
| 6,024,701 A | 2/2000 | Almog |
| 6,115,624 A | 9/2000 | Lewis et al. |

(Continued)

FOREIGN PATENT DOCUMENTS

| TW | I267369 | 12/2006 |
| WO | 0126545 | 4/2001 |
| WO | 0552848 | 6/2005 |

OTHER PUBLICATIONS

"Office Action of Taiwan Counterpart Application", issued on Aug. 17, 2012, p. 1-p. 3, in which the listed references were cited.

(Continued)

*Primary Examiner* — Niketa Patel
*Assistant Examiner* — Lindsey G Hankins
(74) *Attorney, Agent, or Firm* — Jianq Chyun IP Office

(57) ABSTRACT

An apparatus for monitoring fetal positions and fetal movements is provided. The apparatus includes a plurality of sensors, a signal pre-processor, a signal post-processor, and a fetal position judging processor. The sensors are attached on the abdomen of a maternal body to provide at least three measuring leads. The signal pre-processor receives a plurality of sensing signals from the sensors, and the signal pre-processor reduces noises in the sensing signals and amplifies the sensing signals to output a plurality of characteristic sensing signals. The signal post-processor receives the characteristic sensing signals from the signal pre-processor and separates out a plurality of fetal electrocardiograms (FECGs) corresponding to the leads. The fetal position judging processor analyzes the FECGs to obtain a characteristic waveform for each of the FECGs or directly calculates a fetal heart axis vector with respect to a front-side coordinate of the maternal body according to the FECGs.

10 Claims, 38 Drawing Sheets

U.S. PATENT DOCUMENTS

| | | |
|---|---|---|
| 6,340,346 B1 | 1/2002 | Almog et al. |
| 6,658,284 B1 | 12/2003 | Rosen et al. |
| 7,333,850 B2 | 2/2008 | Marossero et al. |
| 7,532,923 B1 | 5/2009 | Hayes-Gill et al. |
| 2005/0267377 A1* | 12/2005 | Marossero et al. ........... 600/511 |
| 2006/0189882 A1 | 8/2006 | Thomas |
| 2007/0088226 A1 | 4/2007 | Spence et al. |
| 2007/0213627 A1 | 9/2007 | James et al. |
| 2008/0125668 A1 | 5/2008 | Graupe et al. |
| 2008/0183092 A1 | 7/2008 | Smith et al. |

OTHER PUBLICATIONS

Kurjak et al., "Fetal Behavior Assessed in All Three Trimesters of Normal Pregnancy by Four-dimensional Ultrasonography," Croat Med J., 2005, pp. 772-780, 46(5).

Govindan et al, "Scaling analysis of paces of fetal breathing, gross-body and extremity movements," Physica A., Dec. 1, 2007, pp. 1-13, 386(1).

Malliani A, et al., "Cardiovascular neural regulation explored in the frequency domain." Circulation 1991; 84: pp. 482-492.

* cited by examiner

APPARATUS AND METHOD FOR MONITORING FETUS IN MATERNAL BODY

CROSS-REFERENCE TO RELATED APPLICATION

This application claims the priority benefit of Taiwan application serial no. 98135638, filed on Oct. 21, 2009. The entirety of the above-mentioned patent application is hereby incorporated by reference herein and made a part of specification.

BACKGROUND OF THE INVENTION

1. Field of the Invention

The present invention generally relates to an apparatus and a method for monitoring a fetus in a maternal body, and more particularly, to an apparatus for monitoring fetal movements, uterine contractions, and fetal positions.

2. Description of Related Art

The utmost concern of a pregnant woman (also referred to as a maternal body) is that whether the baby she's carrying is healthy and growing normally and whether there is the possibility of a premature delivery. Besides consulting a clinical doctor, a mother-to-be can only determine the status of the fetus based on her own observation (for example, by detecting the number of fetal movements). Accordingly, it is very inconvenient to observe and record the status of the fetus for a long time. Thus, a portable equipment that can automatically detect and record the status of a fetus and provide the position, movement, health, and growth of the fetus through data analysis is desired. With such an equipment, the mother-to-be can submit the data measured at home to her clinical doctor to receive better care. As to a maternal body with an abnormal fetal position, it is the best time to correct the fetal position during the $30^{th}$ to the $34^{th}$ weeks of pregnancy. Thus, the portable monitoring equipment should be designed with a fetal position detection function.

Presently, there are many different techniques for monitoring and assessing the health of a fetus before delivery, such as the uterine contraction stress test, the nonstress test, the fetal movement assessment, the biophysical profile, modified biophysical profile (BPP), and the umbilical artery Doppler velocimetry, etc.

In addition, existing techniques for quantitatively analyzing fetal movements include the kick count technique, the Doppler ultrasonic technique, the ultrasonic technique, and the moving coil technique. In the kick count technique, fetal movements are recorded according to the sensation of the maternal body to the fetus. In the Doppler ultrasonic technique, a piezoelectric probe is triggered to emit an ultrasonic wave to a specific area so as to detect the Doppler effect of fetal movements within this area. In the ultrasonic technique, a piezoelectric probe is triggered to emit an ultrasonic wave so as to image the fetus in the abdomen of the maternal body. In the moving coil technique, a moving coil is tied on the abdomen of the maternal body, and when a fetal movement occurs, the moving coil changes by magnetic induction. Each of aforementioned techniques has its own pros and cons.

Moreover, a 4D ultrasonic equipment is the most accurate one among all fetal movement identification equipments and can identify different types of fetal movements. However, a 4D ultrasonic equipment is not suitable for long time use and is very expensive. An abdomen physiological sensor equipment can detect not all but most fetal movements except the respiration of the fetus, and which offers low cost, high portability, and no position adjustment.

FIG. 1 illustrates the basic fetal positions. Referring to FIG. 1(a), the fetus 100 directs its head toward the cervix before delivery so that the head can be delivered first. The fetal position illustrated in FIG. 1(a) is a normal position and which takes up about 96% of all fetal positions. Referring to FIG. 1(b), the fetus 100 has its head directing upwards and his breech directing downwards. This is a very serious abnormal fetal position and takes up about 3% of all fetal positions, and this fetal position needs to be corrected through a complicated process. Referring to FIG. 1(c), the fetus 100 is in a horizontal position. This fetal position takes up about 0.2-0.5% of all fetal positions and is a second serious abnormal fetal position, and which can be corrected through a fetal position correction process some time before the delivery.

FIG. 2 illustrates various directions corresponding to a fetus position. The fetus has different rotation directions. Taking the normal fetal position illustrated in FIG. 1(a) as an example, it has 6 directions including the front and back directions based on the direction of the occipital on the fetus's head. As shown in FIGS. 2(a)-2(f), the 6 directions are respectively denoted as LOP, LOT, LOA, ROP, ROT, and ROA. Similarly, the fetal position illustrated in FIG. 1(b) also has 6 directions. The same method for defining the direction of a fetal position is generally adopted and can be applied to any other fetal position therefore will not be described any further.

FIG. 3 is a cross-sectional view illustrating the directions of a fetal position with respect to a maternal body. Referring to FIG. 3, the maternal body has a backbone 102 and a pelvis 104, and the fetus 106 has a fetal backbone 108. The fetus 106 has different fetal positions according to its direction.

FIG. 4 illustrates a conventional technique of attaching physiological sensors on an abdomen. Referring to FIG. 4, four induction sensors 112 are attached at four different positions of the abdomen 110 of a maternal body. One of the induction sensors 112 is attached under the navel, and the other three induction sensors 112 are respectively attached at a left position, a top position, and a right position, as shown in FIG. 4. An electrocardiogram (ECG) of the fetus can be measured by using the induction sensors 112. FIG. 5 illustrates four conventional electrocardiogram (ECG) categories. An ECG is usually composed of the Q-, R-, and S-waves of the heart, wherein the R-wave is the major analysis object. The wave A in FIG. 5 is an upward triangular wave, the wave B is a downward triangular wave, the wave C is a upward and then downward wave, and the wave D is a downward and then upward wave.

The signal obtained through each measuring lead is categorized into one of the four waveforms illustrated in FIG. 5. Based on clinical data, a fetal position can be obtained by composing the waveforms measured through three measuring leads. A fetal position is categorized according to a combination of several parameters:

X=vertex, brow, face, breech, or shoulder of the fetus
L=left pelvis of the maternal body
R=right pelvis of the maternal body
D=vertical center of the maternal pelvis
A=front half of the maternal pelvis
P=rear half of the maternal pelvis
T=horizontal center of the maternal pelvis A fetal position is the position of a representative bone of a first delivered part in the maternal pelvis (i.e., the front left portion, the front right portion, the rear left portion, and the rear right portion of the pelvis). The representative bone of vertex presentation is the occipital (O), the representative bone of breech presentation is the sacrum (S), the representative bone of face presentation is the mentum (M), and the representative bone of shoulder presentation is the scapula (Sc).

Each fetal position is expressed in following three parts:
1. left (L) or right (L) depending on whether the representative bone is at the left side or right side of the pelvis;
2. the name of the representative bone (for example, "O" with vertex presentation, "S" with breech presentation "M" with face presentation, and "Sc" with shoulder presentation);
3. the representative bone being at the front of, the back of, or across the pelvis (for example, with vertex presentation, the fetal position is determined to be LOA (which is the most common fetal position) if the occipital is at the left side of the pelvis and faces the front side.

Each fetal position is expressed in short as following:
six fetal positions with vertex presentation: LOA, LOT, LOP, ROA, ROT, and ROP.
six fetal positions with breech presentation: LSA, LST, LSP, RSA, RST, and RSP.
six fetal positions with face presentation: LMA, LMT, LMP, RMA, RMT, and RMP.
four fetal positions with shoulder presentation: LScA, LScP, RScA, and RScP.

However, how to improve the conventional technique of attaching physiological sensors on the abdomen of a maternal body so as to monitor a fetus more efficiently and accurately is one of the major subjects in the industry.

SUMMARY OF THE INVENTION

Accordingly, the present invention is directed to an apparatus for monitoring a fetus in a maternal body. The apparatus is portable, can be used for long time monitoring and recording, and requires no position adjustment. A plurality of physiological sensors is attached on the abdomen of the maternal body, and fetal positions and fetal movements are identified through signal pre- and post-processing. The apparatus for monitoring the maternal body and the fetus is formed by using aforementioned information along with uterine contractions, fetal heart rates, and the variations thereof.

The present invention provides a fetal position monitoring apparatus including a plurality of sensors, a signal pre-processor, a signal post-processor, and a fetal position judging processor. The sensors are attached on the abdomen of a maternal body to provide at least three measuring leads. The signal pre-processor receives a plurality of sensing signals from the sensors, and the signal pre-processor reduces noises in the sensing signals and amplifies the sensing signals to output a plurality of characteristic sensing signals. The signal post-processor receives the characteristic sensing signals from the signal pre-processor and separates output fetal electrocardiograms (FECGs) and maternal electrocardiograms (MECGs) corresponding to the measuring leads. The fetal position judging processor analyzes the FECGs to obtain a characteristic waveform for each of the FECGs or directly calculates a fetal heart axis vector with respect to a front-side coordinate of the maternal body according to the FECGs.

The present invention provides a maternal uterine contraction and fetal movement monitoring apparatus for monitoring a maternal body and a fetus. The maternal uterine contraction and fetal movement monitoring apparatus includes a plurality of sensors, a signal pre-processor, a first signal post-processor, a first analysis unit, a second signal post-processor, a second analysis unit, and a third analysis unit. The sensors are attached on the abdomen of the maternal body to provide at least three measuring leads. The signal pre-processor receives a plurality of sensing signals from the sensors, and the signal pre-processor reduces noises in the sensing signals and amplifies the sensing signals to output a plurality of characteristic sensing signals. The first signal post-processor receives the characteristic sensing signals from the signal pre-processor, and the first signal post-processor filters noises out of the characteristic sensing signals to obtain a plurality of information of the maternal body and the fetus, wherein the information includes a MECG signal, a maternal uterine electromyography (EMG) signal, and a FECG signal. The first analysis unit calculates a fetal sympathetic nerve activity signal according to the information obtained by the first signal post-processor. The second signal post-processor receives the characteristic sensing signals from the signal pre-processor and separates out a plurality of FECGs and a plurality of maternal uterine contraction signals corresponding to the measuring leads. The second analysis unit analyzes the FECGs to obtain the FECG and a MECG on each measuring lead, so as to determine whether the fetal position changes, and the second analysis unit obtains a uterine contraction status signal according to the maternal uterine contraction signals. The third analysis unit determines whether there is a fetal movement according to the uterine contraction status signal, the energy variation signals, and the fetal sympathetic nerve activity signal through a fetal movement identification technique, wherein the fetal sympathetic nerve activity signal increases the accuracy in fetal movement detection.

The present invention provides a fetal position monitoring method including following steps. First, a plurality of sensors is attached on the abdomen of a maternal body to provide at least three measuring leads. Then, a plurality of sensing signals is received from the sensors, and a plurality of FECGs and a plurality of MECGs corresponding to the measuring leads are separated out from the sensing signals. Next, the FECGs are analyzed to obtain a characteristic waveform for each of the FECGs, and a plurality of electrocardiogram configurations of the measuring leads is obtained to determine a fetal position. Or, a fetal heart axis vector with respect to a front-side coordinate of the maternal body is directly calculated according to the FECGs.

The present invention provides a maternal uterine contraction and fetal movement monitoring method for monitoring a maternal body and a fetus. First, a plurality of sensors is attached on the abdomen of the maternal body to provide at least three measuring leads. Then, a plurality of sensing signals is received from the sensors, and noises in the sensing signals are reduced and the sensing signals are amplified so as to output a plurality of characteristic sensing signals. Next, the characteristic sensing signals are received, and noises are filtered out of the characteristic sensing signals to obtain a plurality of information of the maternal body and the fetus, wherein the information includes a MECG signal, a maternal uterine EMG signal, and a FECG signal. A fetal sympathetic nerve activity signal is then calculated according to the information. After that, the characteristic sensing signals are received from the signal pre-processor, and a plurality of FECGs and a plurality of maternal uterine contraction signals corresponding to the measuring leads are separated out from the characteristic sensing signals. Next, the FECGs are analyzed to obtain the FECG and a MECG on each of the measuring leads, so as to determine whether the fetal position changes, and a uterine contraction status signal is obtained according to the maternal uterine contraction signals. After that, whether there is a fetal movement is determined according to the uterine contraction status signal, the energy variation signals, and the fetal sympathetic nerve activity signal through a fetal movement identification technique, wherein the fetal sympathetic nerve activity signal increases the accuracy in fetal movement detection.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
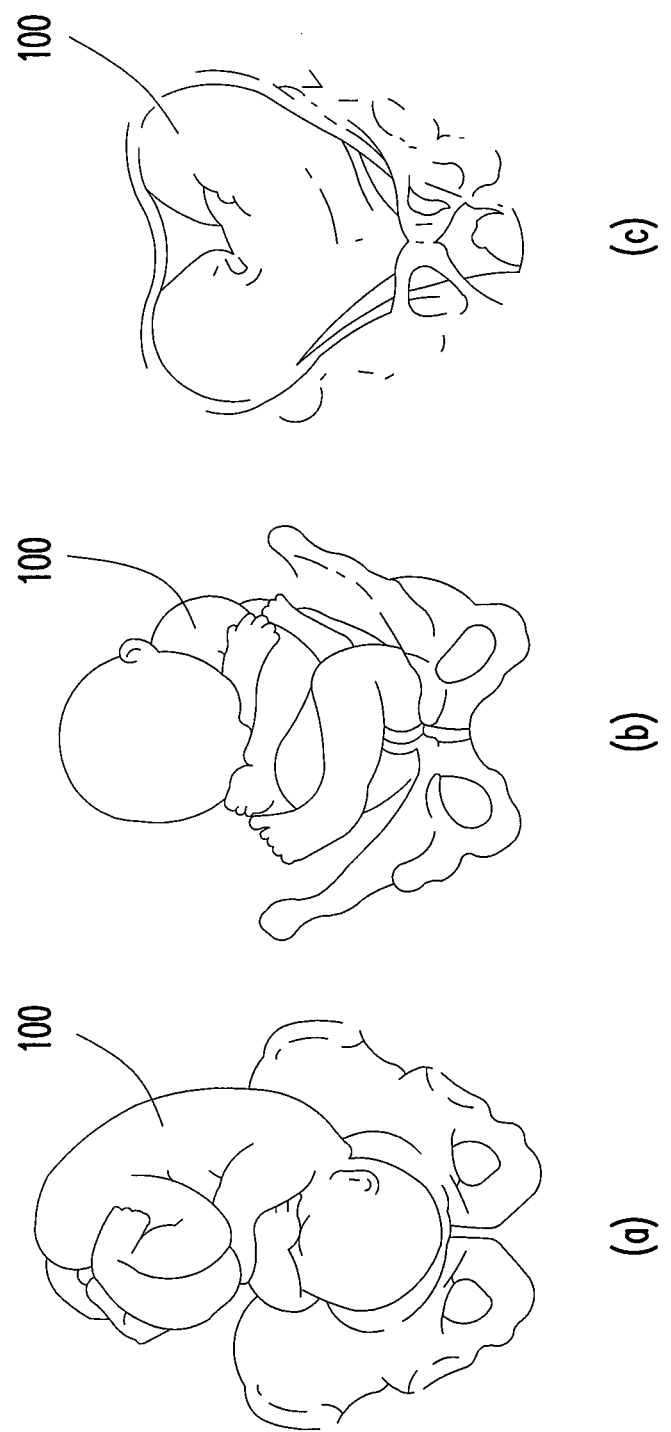
FIG. 1 illustrates the basic fetal positions.

Reference will now be made in detail to the present preferred embodiments of the invention, examples of which are illustrated in the accompanying drawings. Wherever possible, the same reference numbers are used in the drawings and the description to refer to the same or like parts.

In a conventional fetal position identification technique, a doctor touches the abdomen of a maternal body and determines the fetal position based on his own experiences. A more advanced technique is to identify a fetal position through ultrasonic imaging.

In the present invention, a plurality of physiological sensors is attached on the abdomen of a maternal body, and fetal positions and fetal movements are identified through signal pre-processing and post-processing. In the low-cost physiological sensor technique, noises are first filtered out of the signals, and the signals are then separated to obtain uterine contraction and electrocardiogram (ECG) signals of the maternal body and ECG signals of the fetus. The position, movements, and heart rate of the fetus and the uterine contraction and heart rate of the maternal body can be obtained according to foregoing signals through some identification algorithms. With foregoing information, premature delivery and fetal distress can be avoided and the biological block and growth status of the fetus can be understood.

The technique provided by the present invention will be described below with reference to some embodiments of the present invention. However, these embodiments are not intended to limit the scope of the present invention. In addition, the following embodiments can be appropriately combined or integrated with each other.

Generally speaking, the physiological statuses of a maternal body and a fetus are monitored according to the physiological electrical data obtained by a plurality of sensors attached on the abdomen of the maternal body. The uterine contraction and ECG signal measured through each measuring lead are first separated out by using a filter, and the type of FECG in each measuring lead is identified. The FECG in each measuring lead is broken down with respect to the coordinate system of the maternal abdomen and then composed again into a fetal heart axis vector. Namely, a vector sum calculation is performed on the FECG in each measuring lead. After that, the fetal position is identified according to a combination of the FECGs in the measuring leads or the direction of the fetal heart axis projected on the coordinate system of the maternal abdomen. In addition, active fetal movements are identified by using the dynamic variations of the FECGs in the measuring leads, the uterine contraction signals in the measuring leads, and the fetal sympathetic nerve activity signal.

Figure 6:
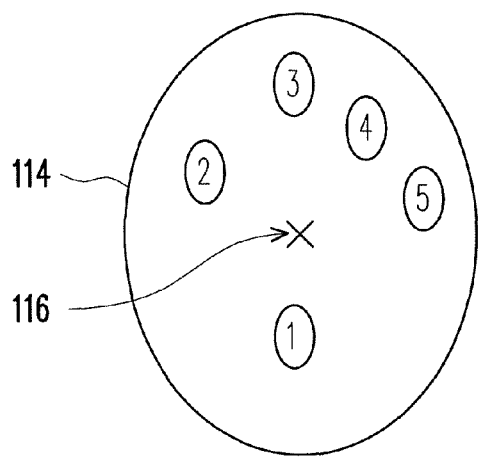
FIG. 6 illustrates the disposition of a plurality of sensors according to an embodiment of the present invention.

In the present invention, multiple sensors (for example, 5 or more electrodes) are adopted. FIG. 6 illustrates the disposition of a plurality of sensors according to an embodiment of the present invention. Referring to FIG. 6, taking 5 sensors as an example, the 5 sensors are attached at the front side of the maternal abdomen 114. With the position of the navel 116 as a reference, the sensor 1 is attached below the navel 116, the sensors 2-4 are respectively attached to the top left of the navel 116, above the navel 116, and to the top right of the navel 116. With the sensor 1 as a reference, the sensors 2-4 form three directive measuring leads. Signals measured through the sensors 1 and 5 are used for reducing noises and separating out MECGs and FECGs.

Figure 7:
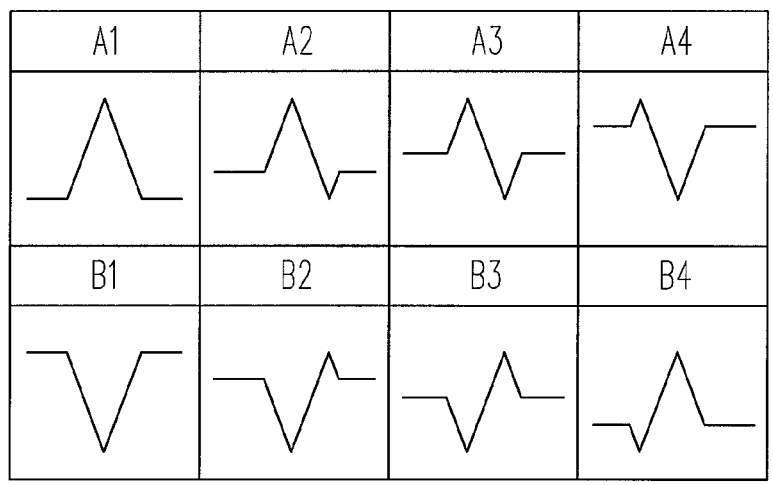
FIG. 7 illustrates different R-waves of fetal electrocardiogram (FECG) according to an embodiment of the present invention.

FIG. 7 illustrates different R-waves of fetal electrocardiogram (FECG) according to an embodiment of the present invention. Referring to FIG. 7, in the present invention, fetal R-waves are respectively measured through the measuring leads formed by the sensors 2-4, and the fetal R-waves have following eight different waveforms A1-A4 and B1-B4:

A1: being an upward triangular wave;

A2: having a front portion as a upward triangular wave and a rear portion as a downward triangular wave, wherein the peak value of the downward triangular wave is smaller than the peak value of the upward triangular wave;

A3: having a front portion as a upward triangular wave and a rear portion as a downward triangular wave, wherein the peak value of the downward triangular wave is about equal to the peak value of the upward triangular wave; and A4: having a front portion as an upward triangular wave and a rear portion as a downward triangular wave, wherein the peak value of the downward triangular wave is greater than the peak value of the upward triangular wave.

In addition, the waveforms B1-B4 include:

B1: being a downward triangular wave;

B2: having a front portion as a downward triangular wave and a rear upward triangular wave, wherein the peak value of the upward triangular wave is smaller than the peak value of the downward triangular wave;

B3: having a front portion as a downward triangular wave and a rear portion as a upward triangular wave, wherein the peak value of the upward triangular wave is about equal to the peak value of the downward triangular wave; and B4: having a front portion as an upward triangular wave and a rear portion as a downward triangular wave, wherein the peak value of the upward triangular wave is greater than the peak value of the downward triangular wave.

In the present invention, the accuracy in fetal position detection is increased through the intermediate states of the waveforms A2, A4, B2, and B4. A mapping table between fetal positions and the R-waves measured through the three measuring leads is established based on clinical data and used for determining a fetal position. Since the waveforms A2, A4, B2, and B4 are transitional waveforms between the waveforms A1, A3, B1, and B3, the accuracy in fetal position detection is increased.

In another method of fetal position determination, energy and vector analysis is performed on the ECGs measured through the three measuring leads to determine a direction of the fetal position. A human ventricle keeps beating to force blood into the artery. In other words, ECG is conducted according to the direction of the heart so that the cardiac muscle contracts to produce a pushing force. Usually the ECG is conducted towards the bottom left of a human body. Thus, after the FECGs are separated out, the pushing direction of the fetal ventricle can be directly analyzed and accordingly the fetal direction can be determined. Besides, since the pushing power can indicate the relation position, the position of the fetus in the maternal abdomen can be roughly determined.

The FECG vectors measured through the three measuring leads are broken down with respect to the coordinate system of the maternal abdomen and then recomposed again to obtain a resultant, and the relative position (for example, at the right side, in the middle, or at the left side) between the fetus and the maternal pelvis can be roughly determined according to relative strengths of the FECGs measured through the three measuring leads.

Figure 8:
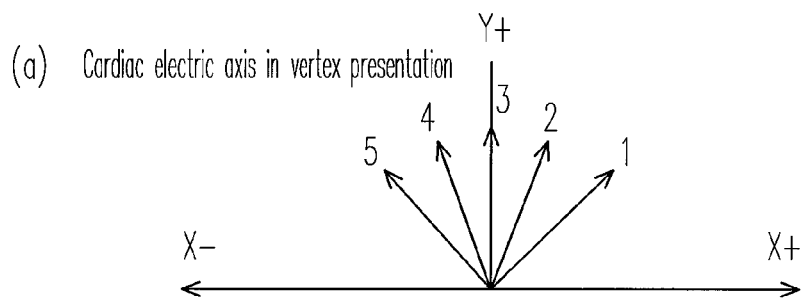
FIG. 8 and FIG. 9 are analysis diagrams of a fetal heart axis according to an embodiment of the present invention.
Figure 8:
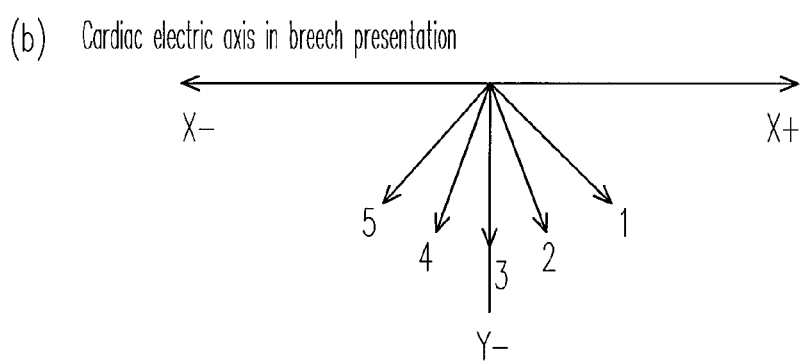
Figure 9:
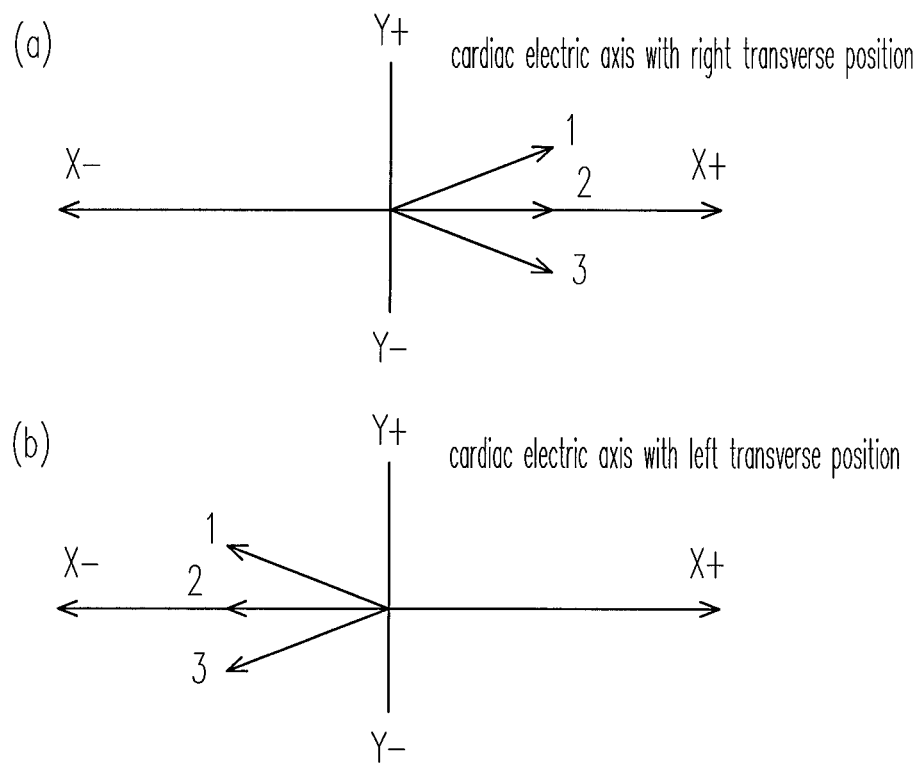

FIG. 8 and FIG. 9 are analysis diagrams of a fetal heart axis according to an embodiment of the present invention. Referring to FIG. 8(a), the FECG resultant on the plane XY of the front-side coordinate of the maternal body is in an upward direction, and which may be equally divided into five areas 1-5 in five directions on the plane XY. However, this is only an embodiment but not intended to limit the present invention. Because the FECG resultant is in the direction of Y+, it is cephalic presentation when the head of the fetus is downward according to the relationship between a ventricle and a normal human body, and the direction indicates the tilt direction of the fetus. Contrarily, referring to FIG. 8(b), it is breech presentation when the breech of the fetus is downward, and the FECG resultant thereof is in the direction of Y−.

Referring to FIG. 9(a), the FECG resultant is at the right transverse position with respect to the front-side coordinate of the maternal body, and which is approximately divided into three area 1-3 in three different directions. FIG. 9(b) illustrates a FECG at the left transverse position.

In other words, through such a method for directly calculating the fetal heart axis vector, the direction of the fetus can be directly measured, so as to determine the fetal position.

Thereafter, besides the fetal position, fetal movement is one indicator of the fetal status, and uterine contraction is one of the important indicators of delivery. Since Braxton Hicks contractions may be caused by fetal movements or other reasons, whether an actual uterine contraction occurs has to be determined. Thus, fetal movements and uterine contractions are also to be measured. The fetal movements and uterine contractions can be detected by processing and analyzing signals measured through the sensors illustrated in FIG. 6. For example, the MECGs and FECGs are separated and then the fetal movements and uterine contractions are determined through other determination mechanisms.

Figure 10:
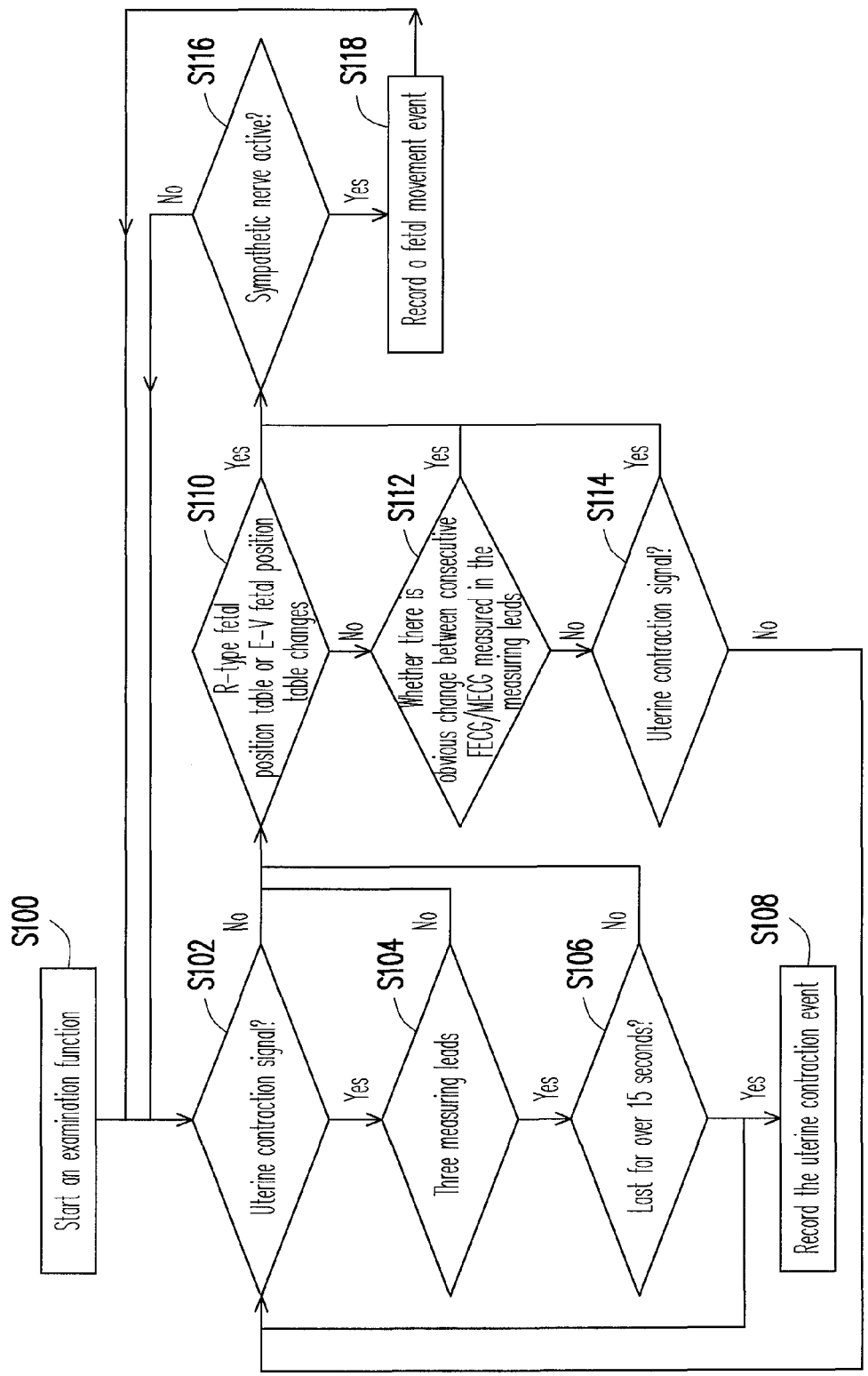
FIG. 10 is a flowchart illustrating how fetal movements and uterine contractions are determined according to an embodiment of the present invention.

FIG. 10 is a flowchart illustrating how fetal movements and uterine contractions are determined according to an embodiment of the present invention. Referring to FIG. 10, in order to increase the accuracy in fetal movement detection, in the present invention, a fetal movement is further detected according to the activity of an automatic nerve system (ANS).

In step S100, an examination function is started. In step S102, a uterine contraction signal is detected. If the uterine contraction signal is detected, step S104 is executed to determine whether a uterine contraction signal is detected in each of the three measuring leads. In step S106, if the uterine contraction signals are detected in the three measuring leads and last for over 15 seconds, it is determined that a uterine contraction actually occurs. In step S108, a uterine contraction event is recorded, and the process then returns to step S102 to continue detecting uterine contractions. If any one of the steps S102, S104, and S106 offers a negative result, step S110 is executed to detect a fetal movement. In step S110, whether the fetal position changes is detected according to whether the mapping table between fetal positions and the R-waves described above changes or whether the fetal heart axis power and vector changes. In step S112, if the fetal position does not change, whether the FECG and MECG signals measured in each measuring lead have obvious change is determined. If the FECG and MECG signals measured in each measuring lead have no obvious change, in step S114, whether a uterine contraction signal is detected is determined. The process returns to step S102 if no uterine contraction signal is detected. If any one of the steps S110, S112, and S114 offers a positive result, step S116 is executed to detect whether a sympathetic nerve is active. If the sympathetic nerve is active, in step S118, a fetal movement is recorded and the process then returns to step S102 to detect the next fetal movement. Contrarily, if the sympathetic nerve is not active, the process also returns to step S102.

The sympathetic nerve activity can be determined in a time domain or a frequency domain with respect to the fetal heart rate chart:

1. time domain determination:
The heart rate raises over several (for example, 15) bpm and lasts for several (for example, 15) seconds;
2. frequency domain determination:
Based on the relationship between automatic nerve system and power spectral density (PSD) disclosed by Malliani A. (Cardiovascular regulation explored in the frequency domain, 1991) (wherein PSD(HF) is a high-frequency spectrum integral and which represents the intensity of a parasympathetic excitation signal, and PSD(LF) is a low-frequency spectrum integral and which represents the intensity of a sympathetic and partial parasympathetic excitation signal), following indexes for indicating the sympathetic nerve activity are further provided by the present invention:

A. it is sympathetic nerve dominant if PSD(LF) exceeds a threshold (i.e. PSD(LF)≧$TH_1$);
B. it is sympathetic nerve dominant if Norm(LF)=PSD(LF)/[PSD(LF)+PSD(HF)] exceeds a threshold (i.e. norm(LF) ≧$TH_2$);
C. the efference of the sympathetic signal increases if PSD (HF) doesn't change and PSD(LF) increases for over a threshold (for example, ΔPSD(LF)≧$TH_3$>0);
D. the efference of the parasympathetic signal decreases if PSD(LF) doesn't change and PSD(HF) decreases for over a threshold (for example, 0>$TH_4$≧ΔPSD(HF)); or
E. the efference of the sympathetic signal increases relatively if ΔPSD(LF)−ΔPSD(HF) increases for over a threshold (for example, ΔSI≧$TH_5$>0).

Figure 11:
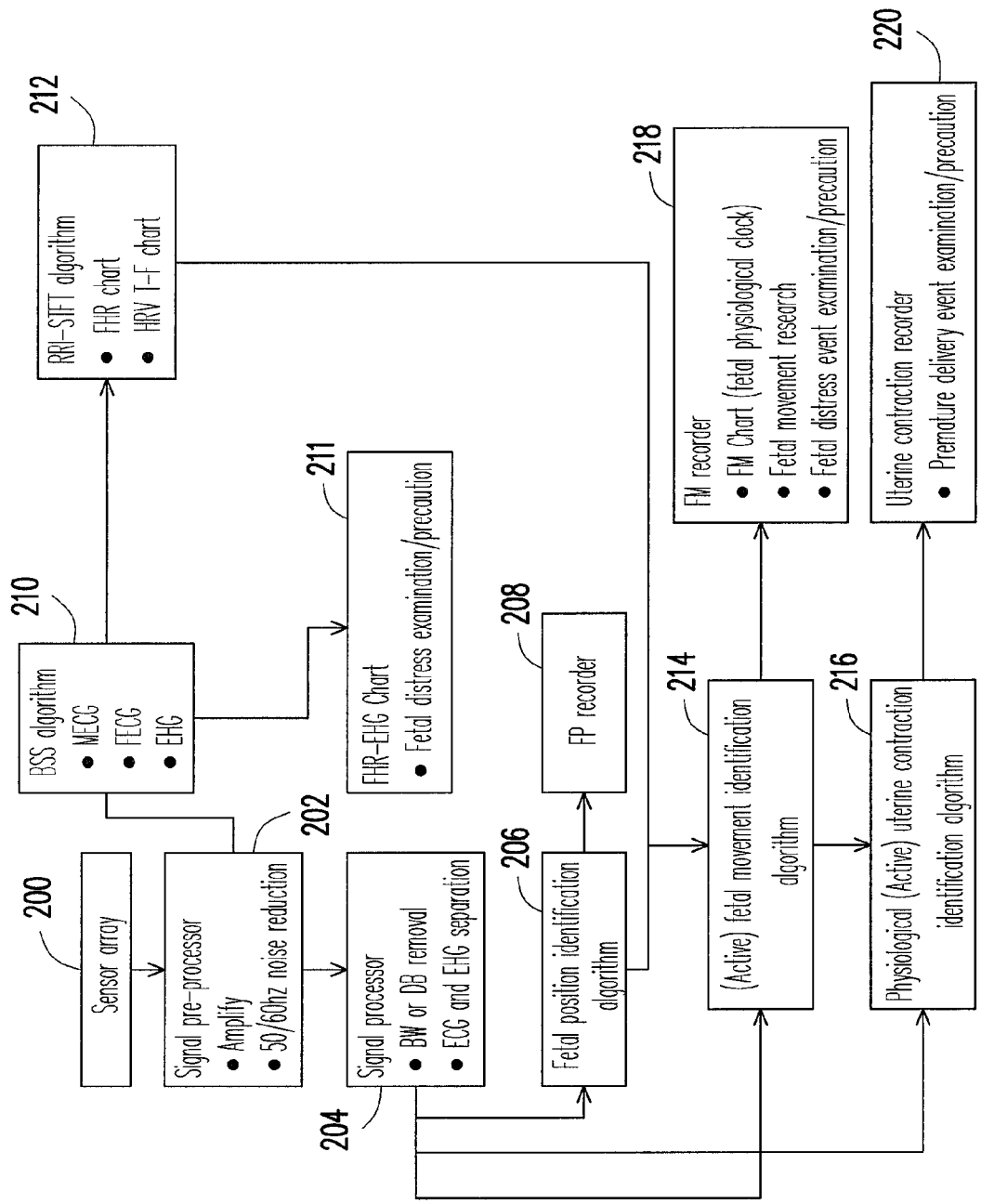
FIG. 11 is a diagram of a maternal uterine contraction and fetal movement monitoring apparatus according to an embodiment of the present invention.

FIG. 11 is a diagram of a maternal uterine contraction and fetal movement monitoring apparatus according to an embodiment of the present invention. Referring to FIG. 11, a sensor array 200 is attached on the abdomen of a maternal body. A signal pre-processor 202 receives the output of the sensor array 200, reduces noises in the output of the sensor array 200, and amplifies the same, wherein the noises reduced are between 50 and 60 Hz. Then, a signal processor 204 receives the output of the signal pre-processor 202, wherein the signal processor 204 removes baseline wander (BW, also referred to as baseline drift (BD)) from the output of the signal pre-processor 202 to obtain the actual signal and separates the ECG signals and the maternal uterine EMG signals (EHGs). The signal processor 204 outputs the processed signal to a fetal position identification unit 206, a fetal movement identification unit 214, and a physiological uterine contraction identification unit 216.

The fetal position identification unit 206 estimates the fetal position according to the fetal position identification algorithm described above. A fetal position (FP) recorder 208 records the fetal position. Meanwhile, the fetal movement identification unit 214 estimates a fetal movement according to the fetal position variation information provided by the fetal position identification unit 206 through a fetal movement identification algorithm, wherein the active state of the sympathetic nerve system is also referred to detect the fetal movement. A fetal movement (FM) recorder 218 records the output of the fetal movement identification unit 214 and performs some data analysis including fetal physiological clock (FM chart), fetal movement research, and fetal distress event examination and precaution. The physiological uterine contraction identification unit 216 performs some calculations (including a physiological active uterine contraction identification algorithm) and outputs the result to a uterine contraction recorder 220, wherein the uterine contraction recorder 220 is used for examining and precautioning a premature delivery event.

The signal pre-processor 202 also outputs to an ECG calculation unit 210 to carry out a blind source separation (BSS) so as to obtain the FECGs, MECGs, and EHGs. The table recording unit 211 records such data as the fetal heart rate (FHR) and the maternal uterine EMG signal (EHG) so as to examine and precaution a fetal distress event. In addition, another calculation unit 212 carries out R-wave examination, heart rate conversion, and heart rate variation analysis to obtain a FHR chart and a heart rate variation (HRV) time-frequency (T-F) chart. The calculation unit 212 outputs its analysis result to the fetal movement identification unit 214 so that the fetal movement identification unit 214 can examine the sympathetic nerve activity according to the analysis result, so as to identify a fetal movement.

Figure 12:
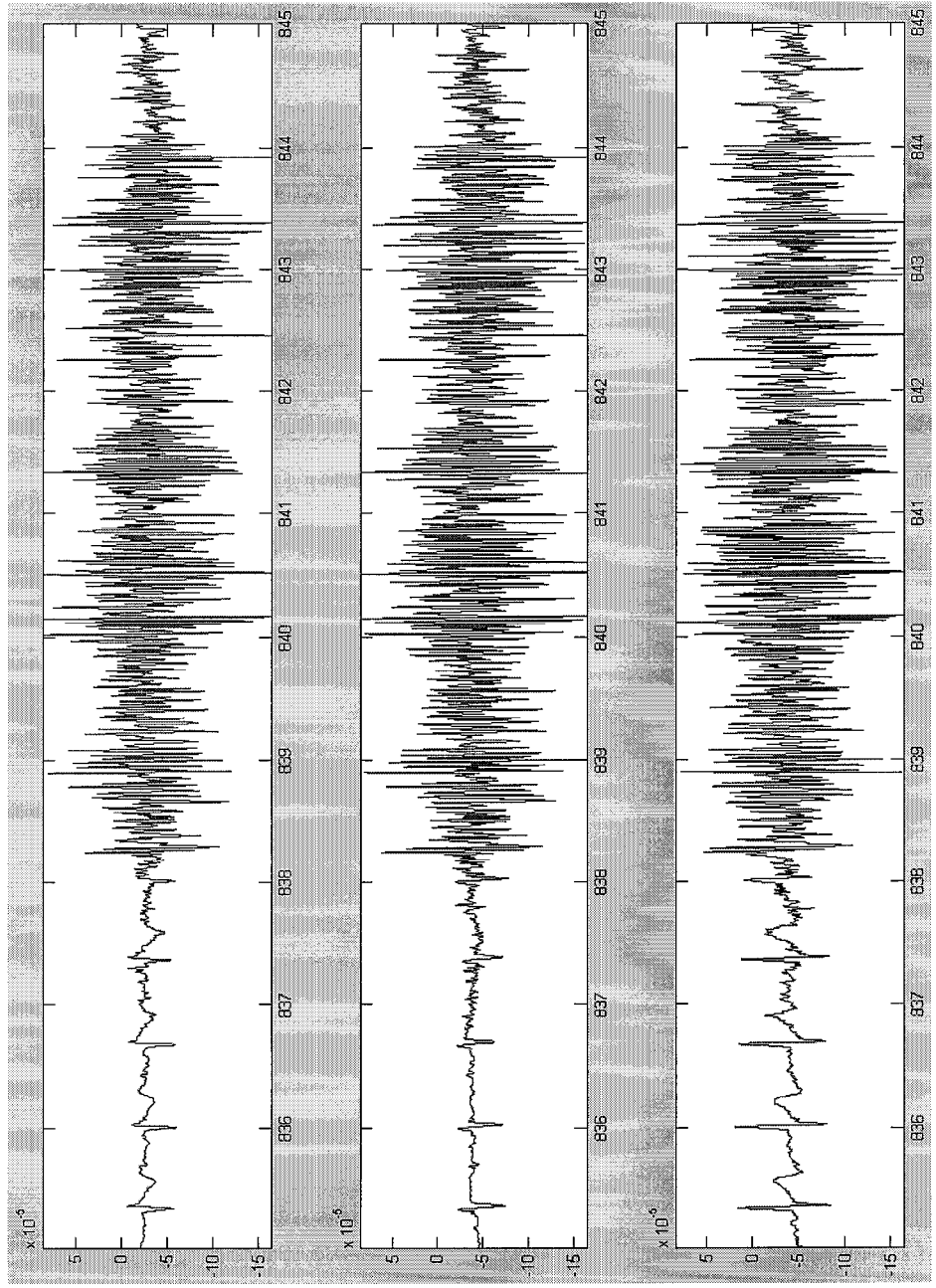
FIG. 12 illustrates signals measured through measuring leads when a physiological uterine contraction actually happens according to an embodiment of the present invention.

FIG. 12 illustrates signals measured through measuring leads when a physiological uterine contraction actually happens according to an embodiment of the present invention. Referring to FIG. 12, uterine contraction signals are detected in the three MECG measuring leads and last for over 15 seconds. Accordingly, it is determined that a physiological uterine contraction occurs.

Figure 13:
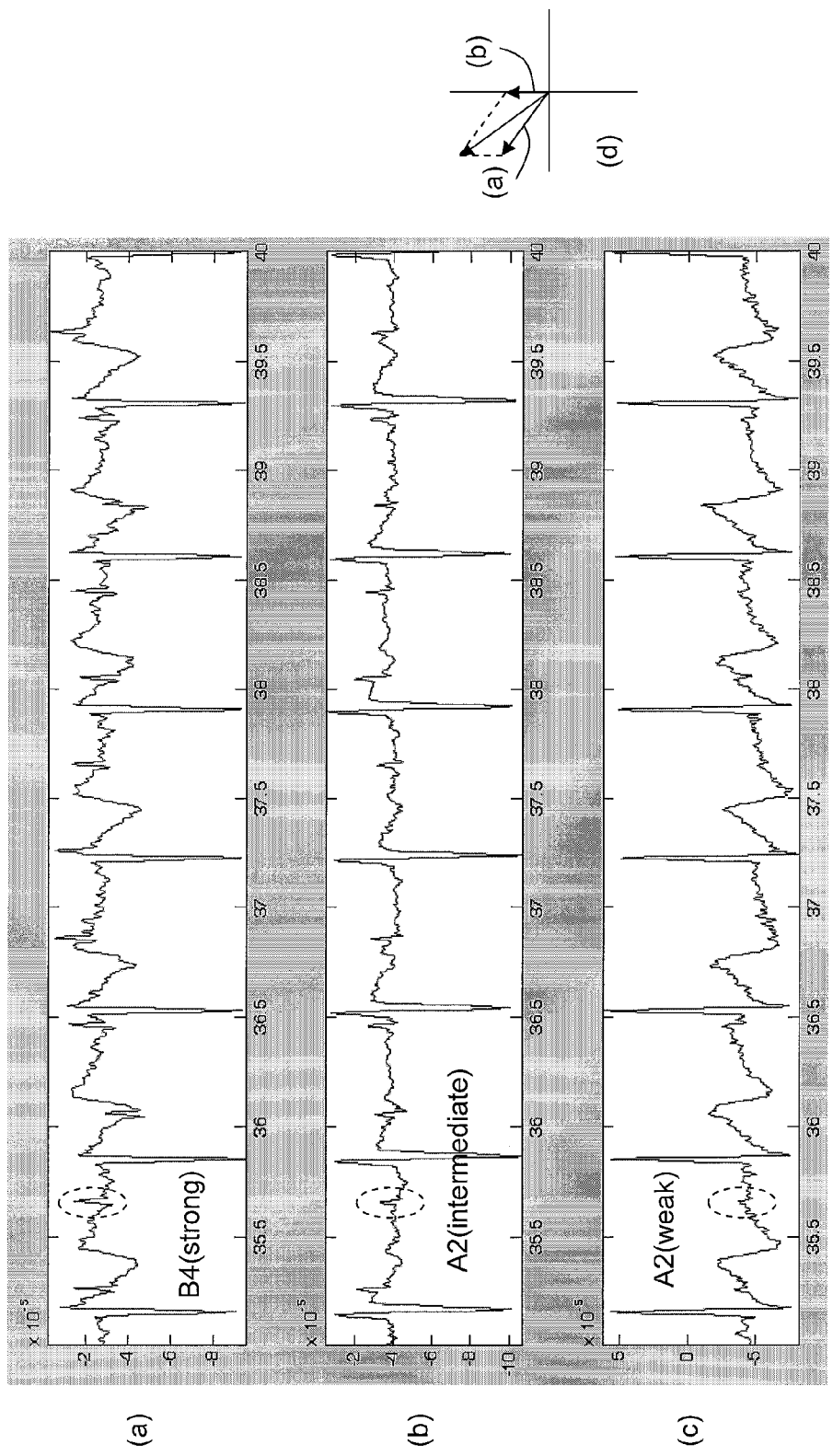
FIG. 13 illustrates two fetal position determining methods according to an embodiment of the present invention.

FIG. 13 illustrates two fetal position determining methods according to an embodiment of the present invention. Referring to FIG. 13, the FECG signals measured through the three measuring leads include a FECG signal a in the measuring lead 1, a FECG signal b in the measuring lead 2, and a FECG signal c in the measuring lead 3, wherein the FECG signal a in the measuring lead 1 is the strongest signal while the FECG signal c in the measuring lead 3 is the weakest. The fetal R-waves in the three measuring leads are illustrated in FIG. 13. Corresponding to the R-waves illustrated in FIG. 7, the waves measured in the three measuring leads respectively have the waveforms B4, A2, and A2, and the intensities thereof are respectively strong, intermediate, and weak. In the first fetal position detection method, the fetal position is cephalic presentation. In addition, the same fetal position can be determined according to the energy and vector analysis on the fetal R-waves. It can be further determined that the fetal heart is located at the right side of the maternal pelvis. As shown in FIG. 13(d), a resultant of the signal a measured in the measuring lead 1 and the signal b measured in the measuring lead 2 is obtained through analysis on the fetal heart axis vector and determined with respect to the direction of the fetal heart axis.

Figure 2:
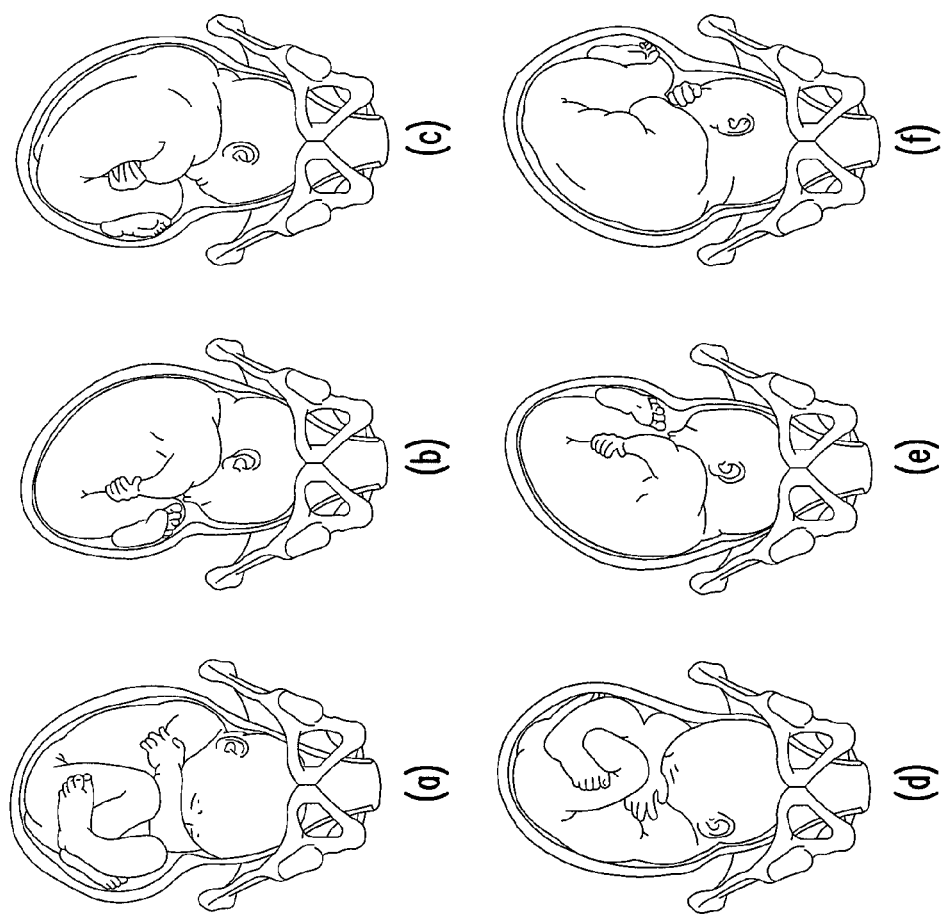
FIG. 2 illustrates various directions corresponding to a fetus position.
Figure 14:
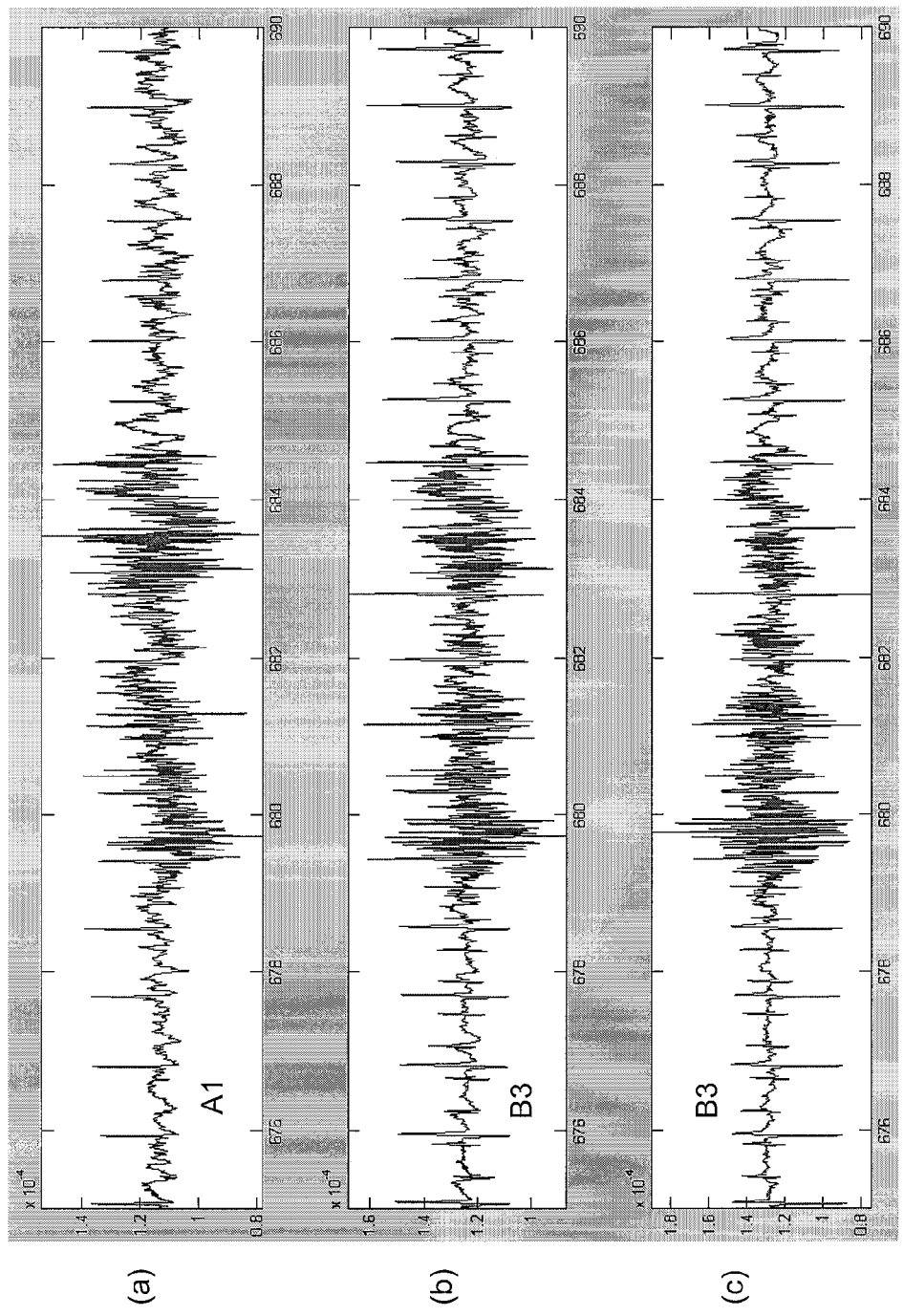
FIG. 14 illustrates a Braxton Hicks contraction caused by a body stretch according to an embodiment of the present invention.

FIG. 14 illustrates a Braxton hicks contraction caused by a body stretch according to an embodiment of the present invention. Referring to FIG. 14, uterine contraction signals are detected in all three measuring leads but they last less than 15 seconds. Accordingly, it is determined that a Braxton Hicks contraction occurs. Besides, the waveforms of the fetal R-waves are respectively the waveforms A1, B3, and B3, and the intensities thereof are respectively weak, strong, and intermediate, and the fetal position is determined to the a LOT cephalic presentation, as shown in FIG. 2(b).

Figure 15:
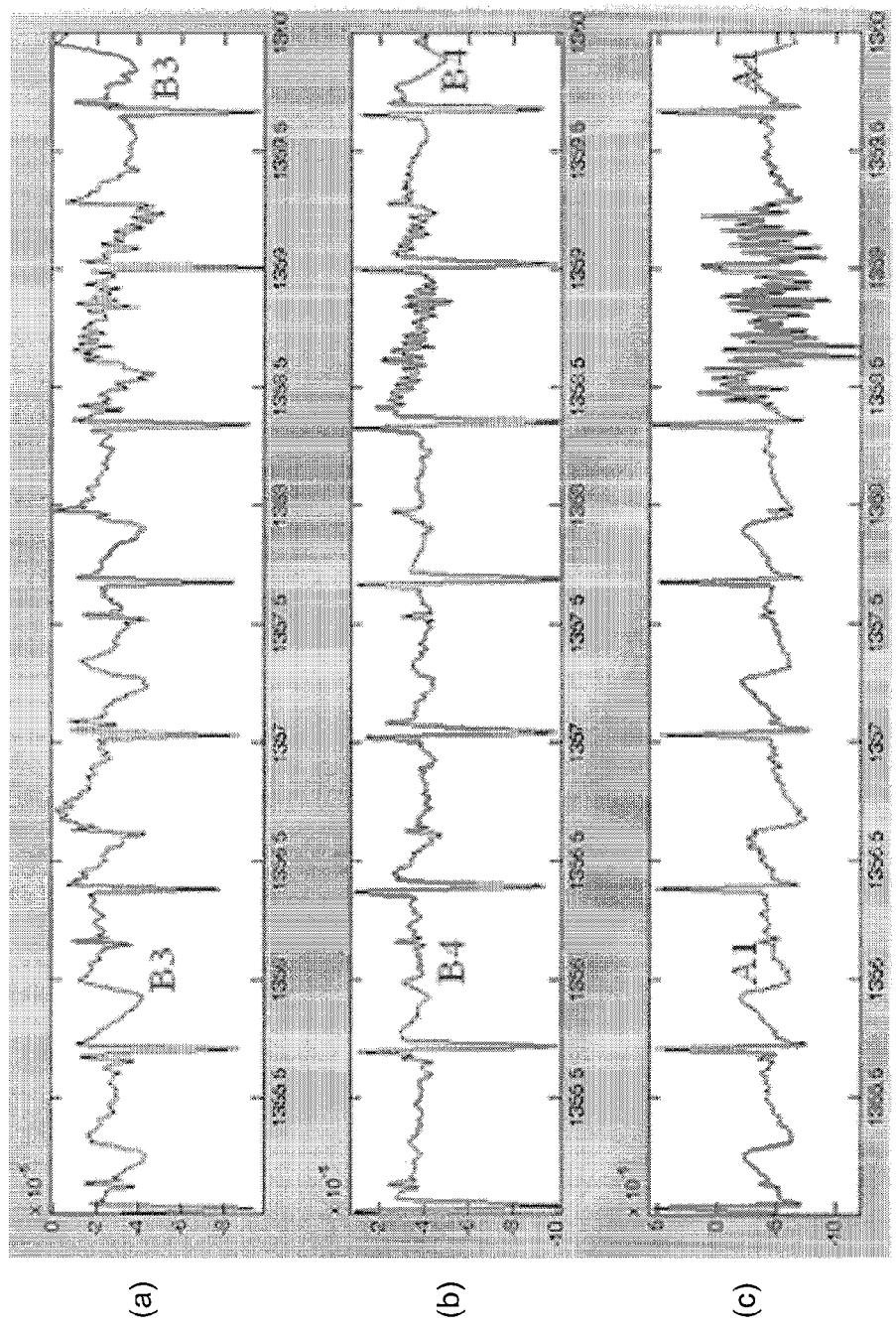
FIG. 15 illustrates the signals of a fetal position and a kicking fetal movement according to an embodiment of the present invention.

FIG. 15 illustrates the signals of a fetal position and a kicking fetal movement according to an embodiment of the present invention. Referring to FIG. 15, a uterine contraction signal is only detected in the measuring lead 3, and only faint uterine contraction signals are detected in the other two measuring leads. The waveforms of the fetal R-waves are respectively the waveforms B3, B4, and A1, and the intensities thereof are respectively strong, intermediate, and weak. The fetal position is determined to be the LOP cephalic presentation, as shown in FIG. 2(a). This is one of the Braxton Hicks contractions, and it can be further determined that whether this is a kicking fetal movement.

Figure 16:
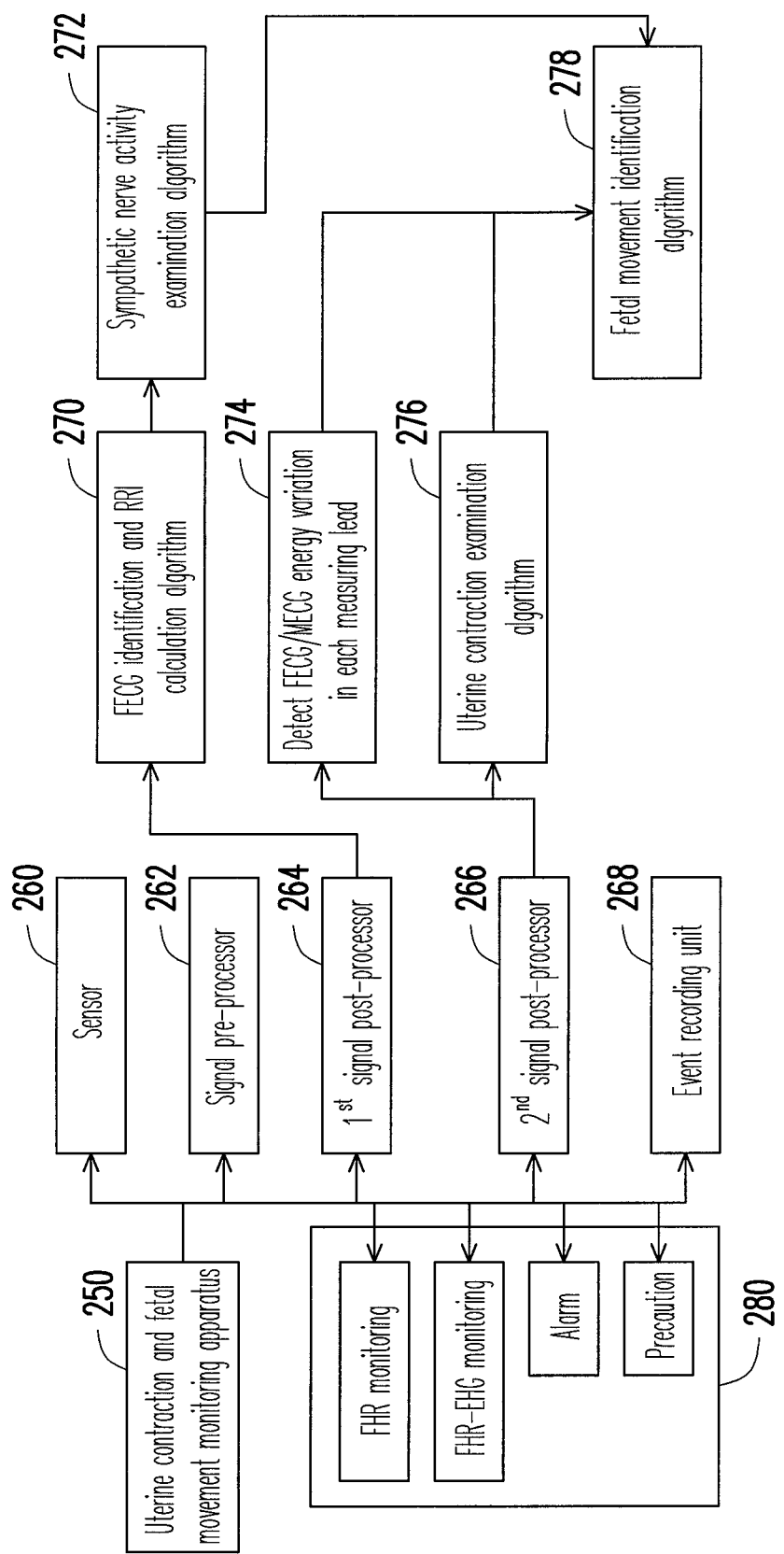
FIG. 16 illustrates the structure of a maternal uterine contraction and fetal movement monitoring apparatus according to an embodiment of the present invention.

FIG. 16 illustrates the structure of a maternal uterine contraction and fetal movement monitoring apparatus according to an embodiment of the present invention. Referring to FIG. 16, the uterine contraction and fetal movement monitoring apparatus 250 includes a plurality of sensors 260, a signal pre-processor 262, a first signal post-processor 264, and a second signal post-processor 266, and the uterine contraction and fetal movement monitoring apparatus 250 may further include an event recording unit 268 and a monitoring and alarm unit 280.

The sensors 260 are attached on the abdomen of a maternal body to provide at least three measuring leads. There may be at least 5 sensors 260. The signal pre-processor 262 receives a plurality of sensing signals from the sensors 260, and the signal pre-processor 262 reduces noises in the sensing signals and amplifies the sensing signals to output a plurality of characteristic sensing signals. The first signal post-processor 264 receives the characteristic sensing signals from the signal pre-processor and analyzes the characteristic sensing signals to obtain a plurality of information of the maternal body and the fetus, wherein the information includes a MECG signal, a maternal uterine EMG signal, and a FECG signal.

The first analysis unit includes analysis blocks 270 and 272. The analysis block 270 identifies FECGs and calculates RRIs according to the information obtained by the first signal post-processor 264, and the analysis block 272 calculates a fetal sympathetic nerve activity signal.

The second signal post-processor 266 receives the characteristic sensing signals from the signal pre-processor 262 and reduces BD in the characteristic sensing signals to separate out a plurality of FECGs and a plurality of maternal uterine contraction signals corresponding to the measuring leads.

The second analysis unit includes analysis blocks 274 and 276, wherein the analysis blocks 274 and 276 receive the output signals of the second signal post-processor 266. The analysis block 274 analyzes the FECGs to obtain the energy variation of the FECG in each measuring lead with respect to a MECG so as to monitor body shifting fetal movements. Besides, the analysis block 276 analyzes the uterine contraction of the maternal body to obtain a uterine contraction status signal.

The third analysis unit 278 determines whether there is a fetal movement according to the uterine contraction status signal, the energy variation signals, and the fetal sympathetic nerve activity signal through a fetal movement identification technique, wherein the fetal sympathetic nerve activity signal is adopted for increasing the accuracy of fetal movement detection.

Figure 17:
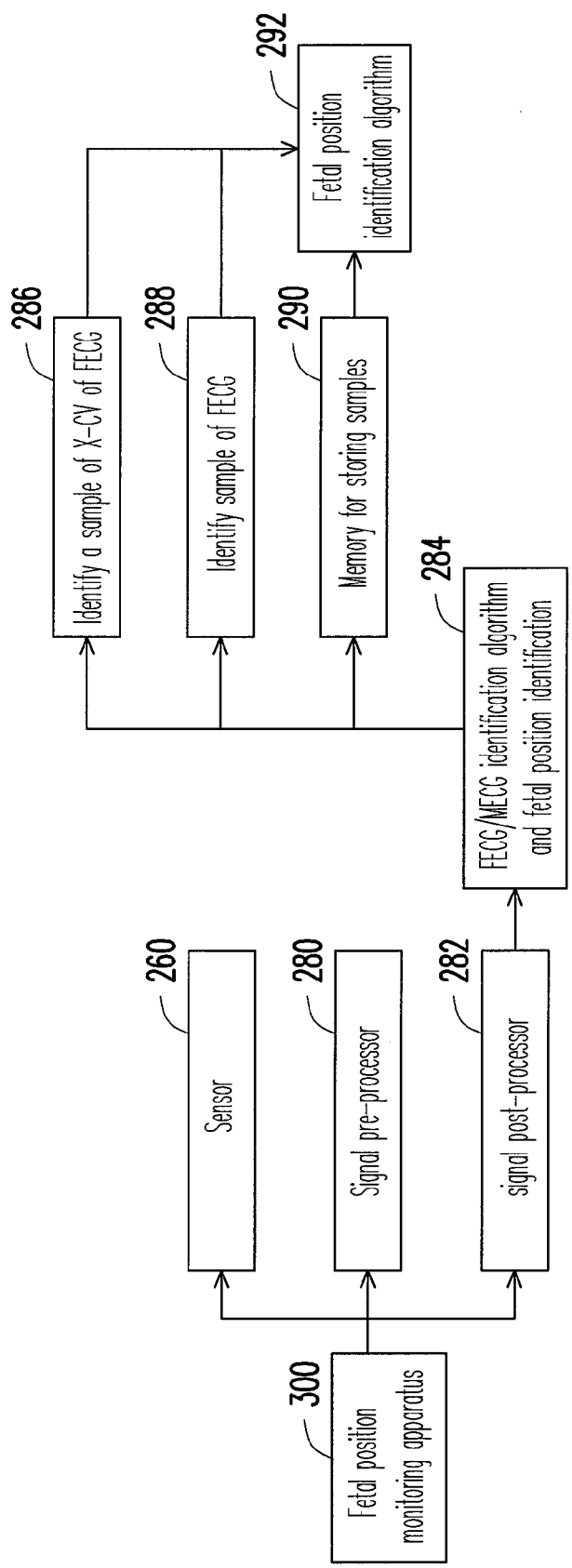
FIG. 17 illustrates the structure of a fetal position monitoring apparatus according to an embodiment of the present invention.

FIG. 17 illustrates the structure of a fetal position monitoring apparatus according to an embodiment of the present invention. Referring to FIG. 17, the fetal position monitoring apparatus 300 includes a plurality of sensors 260, a signal pre-processor 280, a signal post-processor 282, and a fetal position judging processor 284. The sensors 260 are attached on the abdomen of a maternal body to provide at least three measuring leads. The signal pre-processor 280 receives a plurality of sensing signals from the sensors 260 and reduces noises in the sensing signals and amplifies the sensing signals to output a plurality of characteristic sensing signals. The signal post-processor 282 receives the characteristic sensing signals from the signal pre-processor 280 and separates out a plurality of FECGs corresponding to the measuring leads. The fetal position judging processor 284 analyzes the FECGs to obtain a characteristic waveform of each FECG in the measuring leads and determines the fetal position through table lookup.

In addition, the fetal position judging processor 284 can be connected to other analysis blocks 286, 288, 290, and 292 to carry out a different fetal position identification method. To be specific, the fetal position judging processor 284 directly calculates a fetal heart axis vector with respect to a front-side coordinate of the maternal body according to the energy and vectors of the FECGs, so as to determine the location of the fetal heart. Thus, the fetal position can be directly calculated. The analysis block 286 identifies a sample (X-CV) of the energy drift X of the FECG (X indicates that whether the FECG energy leans toward the left side, right side, or in the middle of the maternal pelvis) and the fetal heart axis vector (CV). The analysis block 286 identifies a simple of the FECG. The analysis block 290 is a memory for storing the samples. The analysis block 292 analyzes the data of the analysis blocks 286 and 290 to obtain the fetal position.

Figure 18:
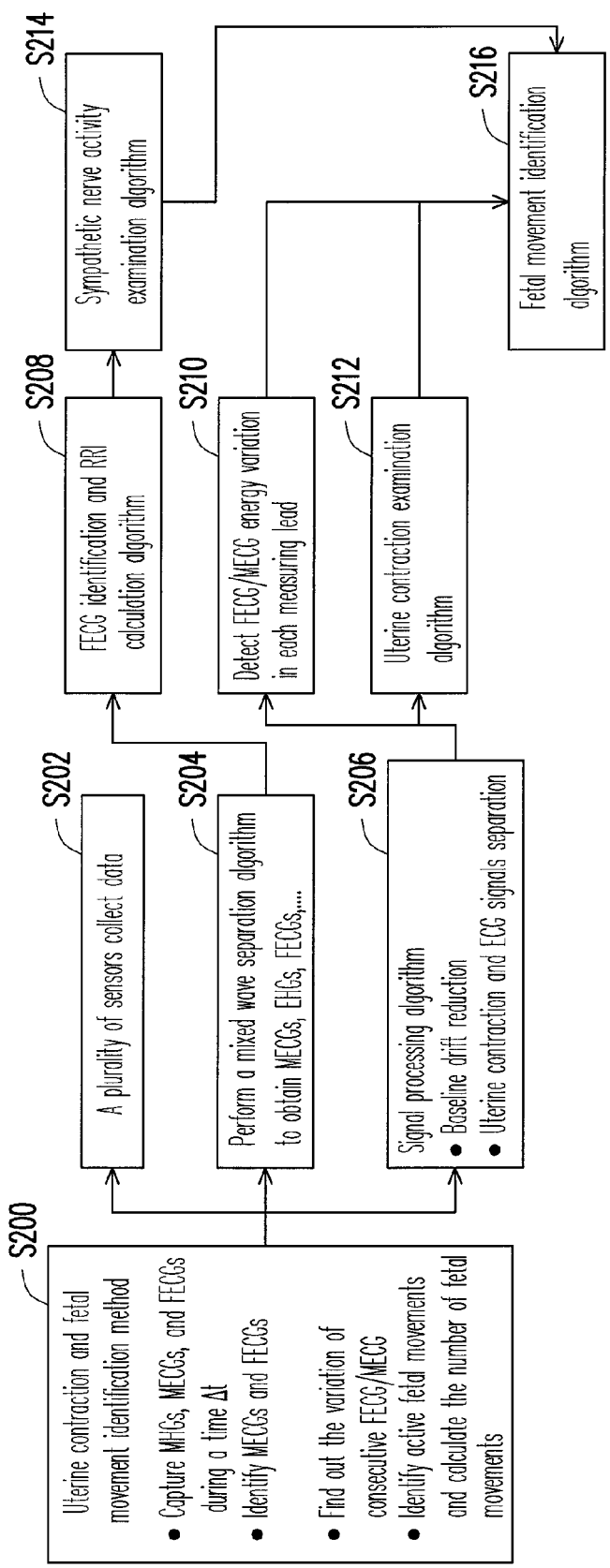
FIG. 18 illustrates a maternal uterine contraction and fetal movement identification method according to an embodiment of the present invention.

FIG. 18 illustrates a maternal uterine contraction and fetal movement identification method according to an embodiment of the present invention. Referring to FIG. 18, in the uterine contraction and fetal movement identification method S200, first, EHG signals, MECG signals, and FECG signals are captured during a period. Then, the MECGs and FECG are identified. Next, a variation of consecutive FECG/MECG is detected. After that, an active fetal movement is identified and the number of fetal movements is calculated. The uterine contraction and fetal movement identification method S200 may have a plurality of steps. In step S202, data is collected by using a plurality of electrodes. In step S204, MECG signals, EHG signals, and FECG signals are obtained through a BSS algorithm. In step S206, BD in the signals is reduced, and uterine contraction signals and ECG signals are separated.

Thereafter, in step S208, the FECGs are identified and RRI is calculated. Then, in step S214, the sympathetic nerve activity is estimated through a sympathetic nerve activity examination algorithm. Next, in step S210, the energy variation of each FECG/MECG in the measuring leads is detected, and in step S212, a uterine contraction analysis is performed through a uterine contraction algorithm. In step S216, whether a fetal movement occurs is determined according to the result obtained in foregoing steps through a fetal movement identification algorithm.

Figure 19:
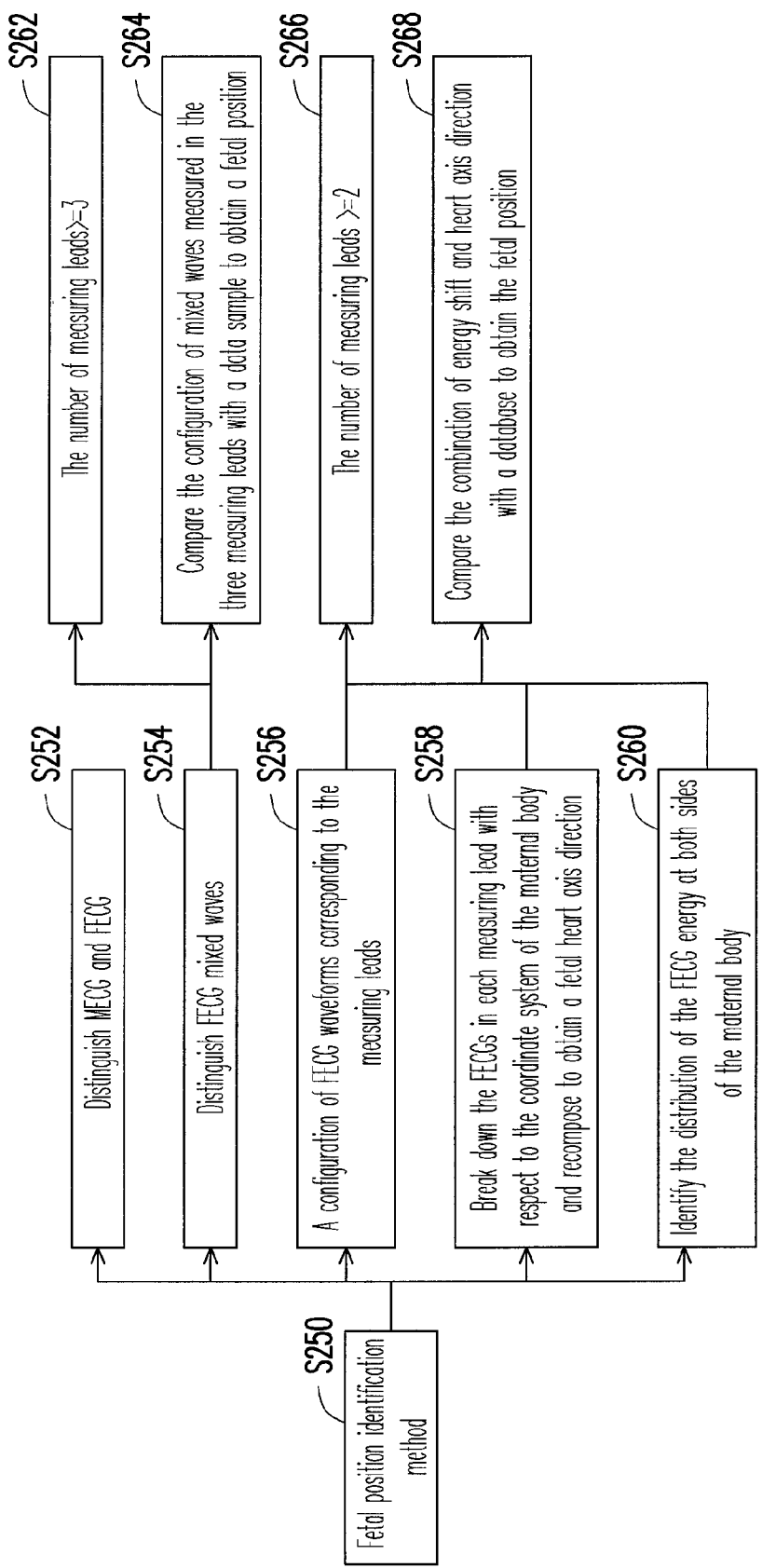
FIG. 19 illustrates a fetal position identification method according to an embodiment of the present invention.

FIG. 19 illustrates a fetal position identification method according to an embodiment of the present invention. Referring to FIG. 19, the fetal position identification method S250 is to determine the direction of the fetus in the abdomen of the maternal body, and which includes a plurality of steps. In step 252, the MECGs and the FECGs are separated. In step 254, the FECGs are separated. In step S256, the configuration of the R-waves in the FECGs corresponding to the measuring leads is analyzed. After that, in step S262, signals in the three measuring leads are obtained, and in step S264, the configuration of the R-waves in the three measuring leads is compared with a data sample to obtain a fetal position. This is the first fetal position detection method.

According to another fetal position detection method, in step S258, the FECG vectors corresponding to the measuring leads are broken down with respect to the coordinate system of the maternal body and recomposed again to obtain a fetal heart axis direction. In step S260, the distribution of the FECG energy at both sides of the maternal body is determined. Thereafter, in step S266, the signals in at least two measuring leads are obtained and analyzed. In step S268, a fetal position is obtained by comparing a combination of energy drift and the fetal heart axis direction with a database.

Figure 20:
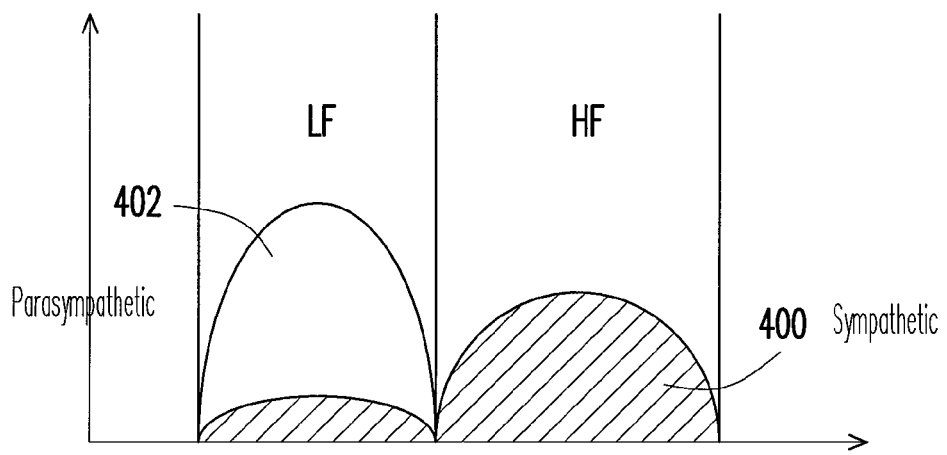
FIGS. 20-23 illustrate the variations of a sympathetic nerve and a parasympathetic nerve in a frequency spectrum according to embodiments of the present invention.

FIGS. 20-23 illustrate the variations of a sympathetic nerve and a parasympathetic nerve in a frequency spectrum according to embodiments of the present invention. Referring to FIG. 20, the spectrum of the parasympathetic nerve 400 has a high frequency (HF) portion and a low frequency (LF) portion, and the spectrum of the sympathetic nerve 402 has only a low frequency portion. PSD(LF) refers to the total of the LF portion, and PSD(HF) refers to the total of the HF portion. Thus, while determining the sympathetic nerve activity, it is determined to be sympathetic nerve dominant if PSD(LF) exceeds a threshold (for example, PSD(LF)$\geqq$TH$_1$). Or it is determined to be sympathetic nerve dominant if norm(LF)= PSD(LF)/[PSD(LF)+PSD(HF)] exceeds a threshold (for example, norm(LF)$\geqq$TH$_2$).

Figure 21:
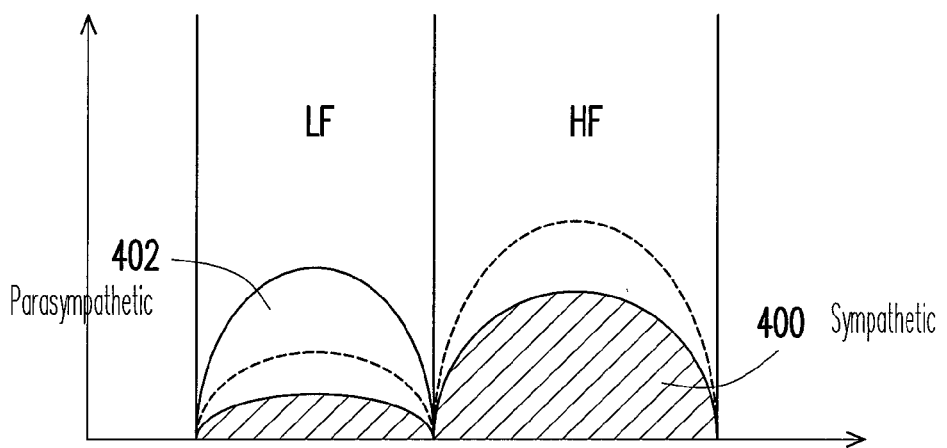

Referring to FIG. 21, in another situation, when PSD(LF) does not change compared to the previous spectrum, it remains at the same solid line, but PSD(HF) decreases from the dotted line to the solid line of the parasympathetic nerve 400. Because the variation of PSD(HF) is caused by the variation of the parasympathetic nerve 400, the LF portion thereof is expected to decrease from the dotted line to the solid line of the parasympathetic nerve 400. Herein since PSD(LF) does not change, it can be determined that the variation of the sympathetic nerve 402 is the value between the dotted line and the solid line of the parasympathetic nerve 400. Thus, the determination condition can be set as that the parasympathetic signal efference decreases if PSD(LF) doesn't change and PSD(HF) decreases for over a threshold (for example, $0 > TH_4 \geq \Delta SD(HF)$).

Figure 22:
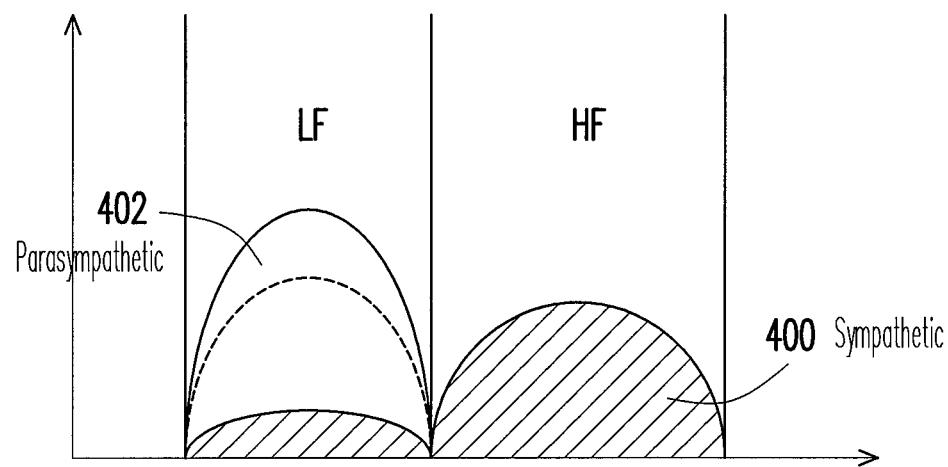

Referring to FIG. 22, when PSD(HF) does not change while PSD(LF) changes (for example, PSD(LF) increases from the dotted line to the solid line), it is determined that the signal efference of the sympathetic nerve 402 increases. The determination condition can be set as that the sympathetic signal efference increases if PSD(HF) does not change and PSD(LF) increases for over a threshold (for example, $\Delta PSD(LF) \geq TH_3 > 0$).

Figure 23:
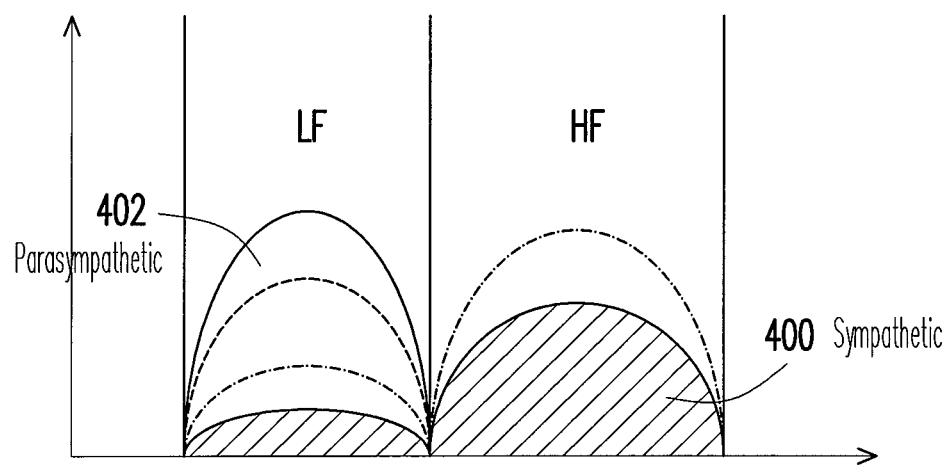
Figure 24:
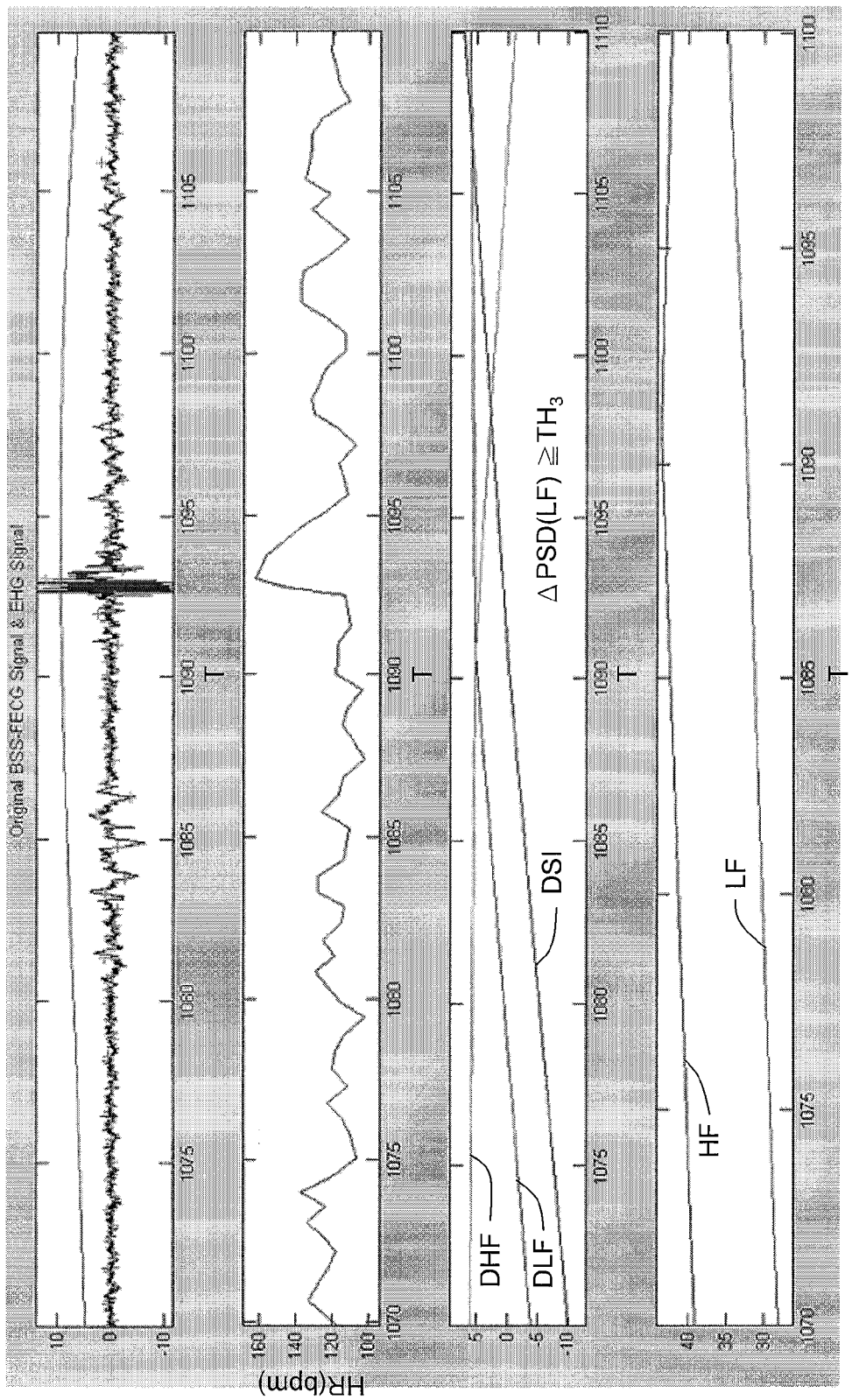
FIGS. 24-43 illustrate the measurements of four signals according to embodiments of the present invention.
Figure 25:
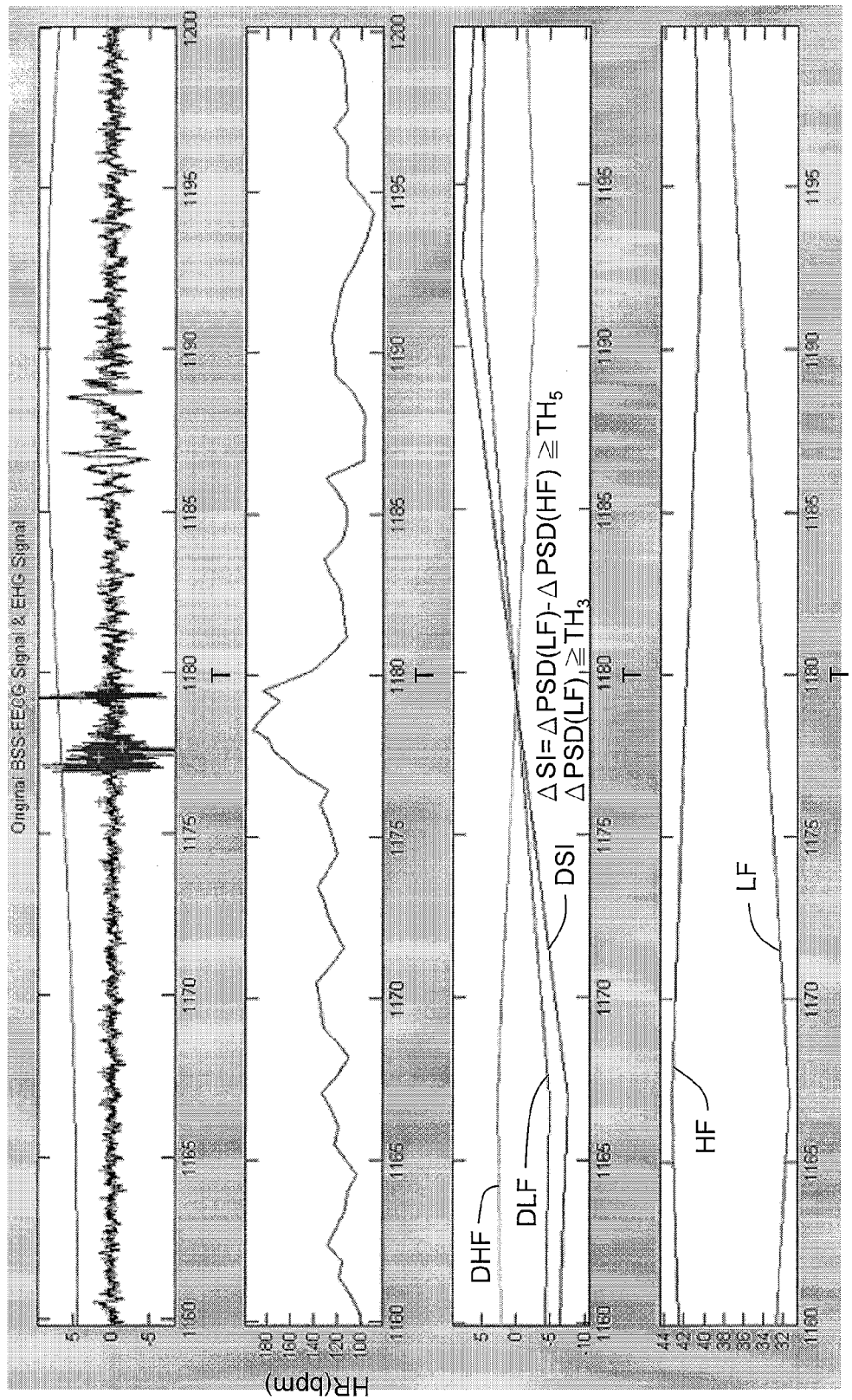
Figure 26:
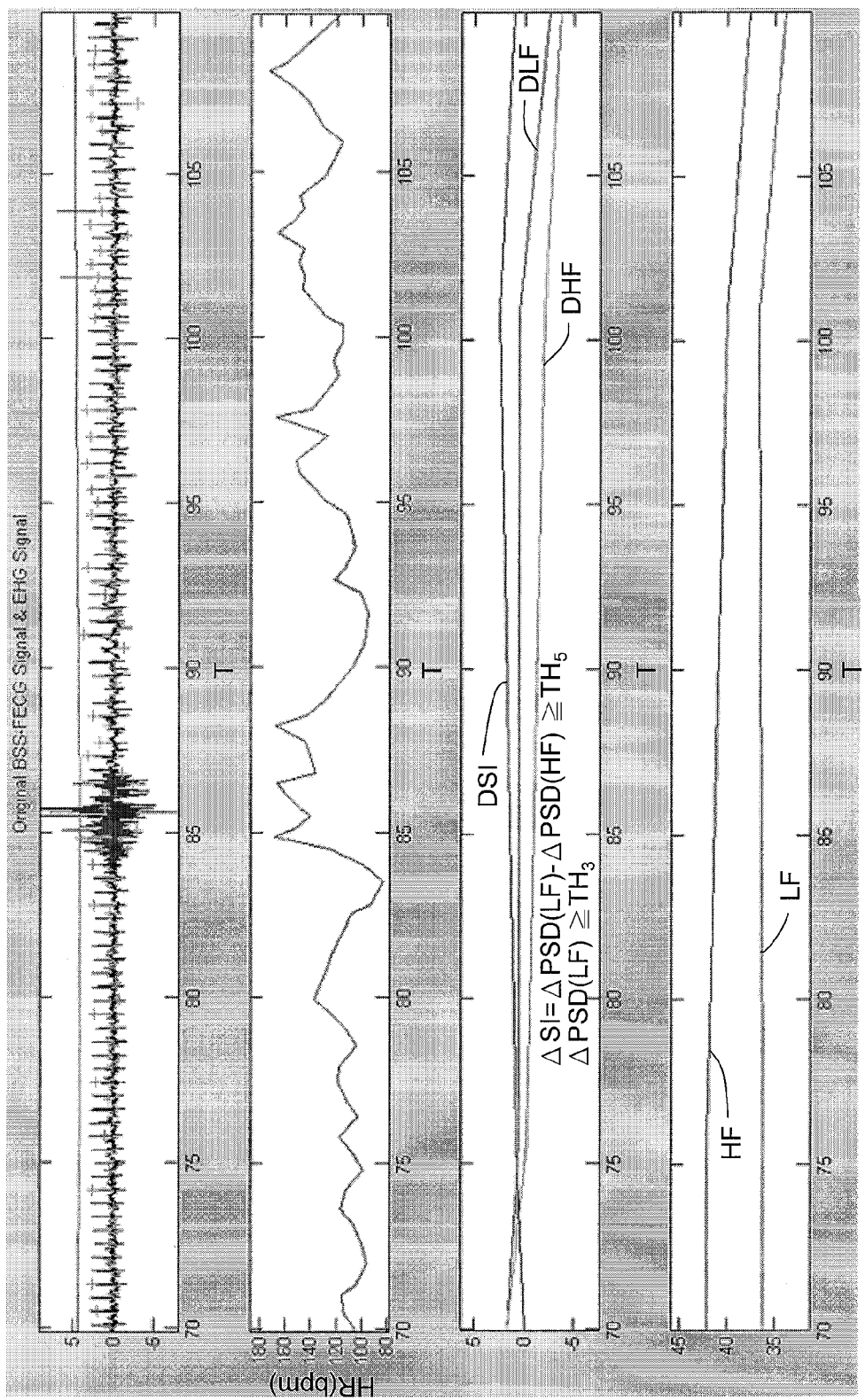
Figure 27:
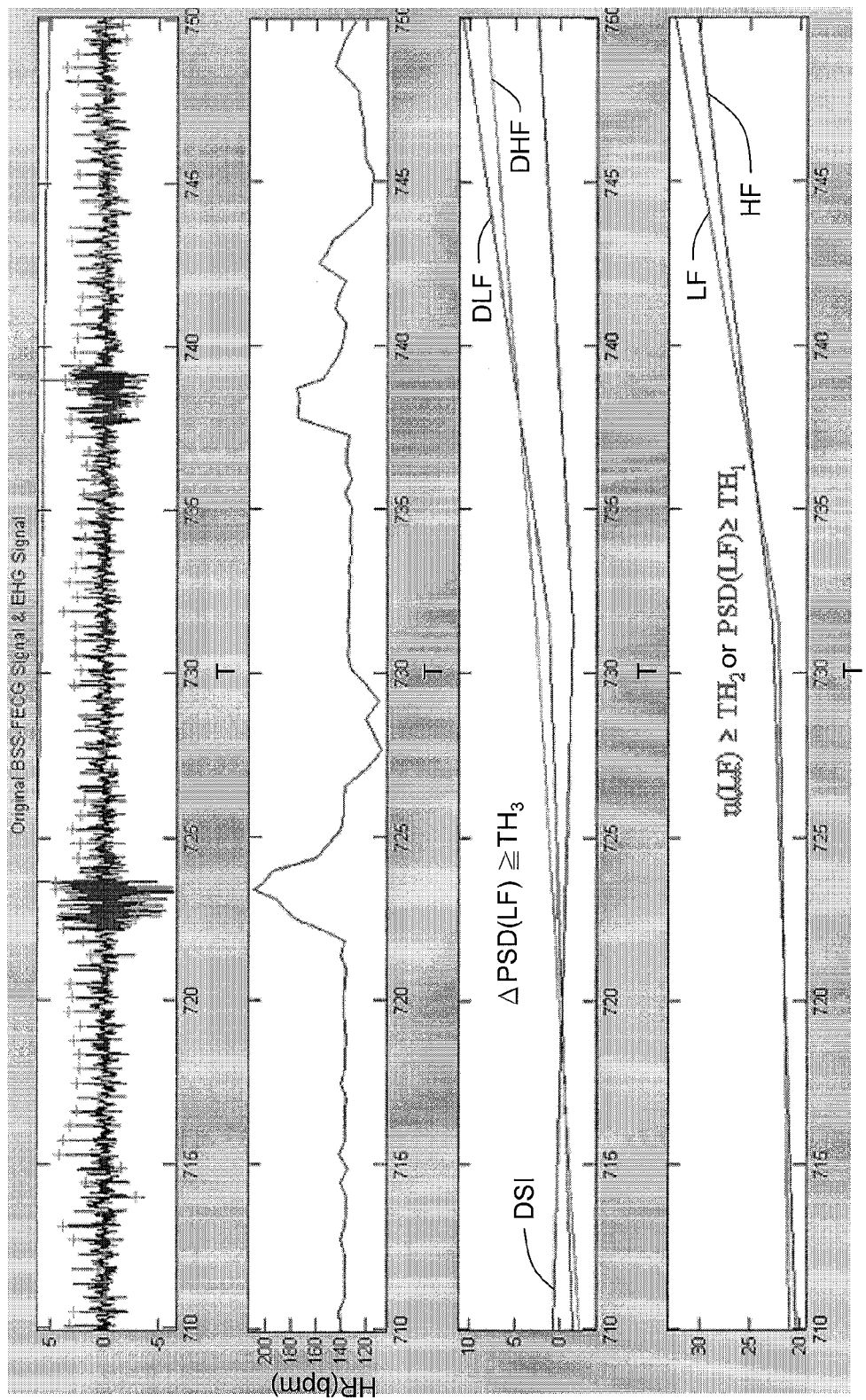
Figure 28:
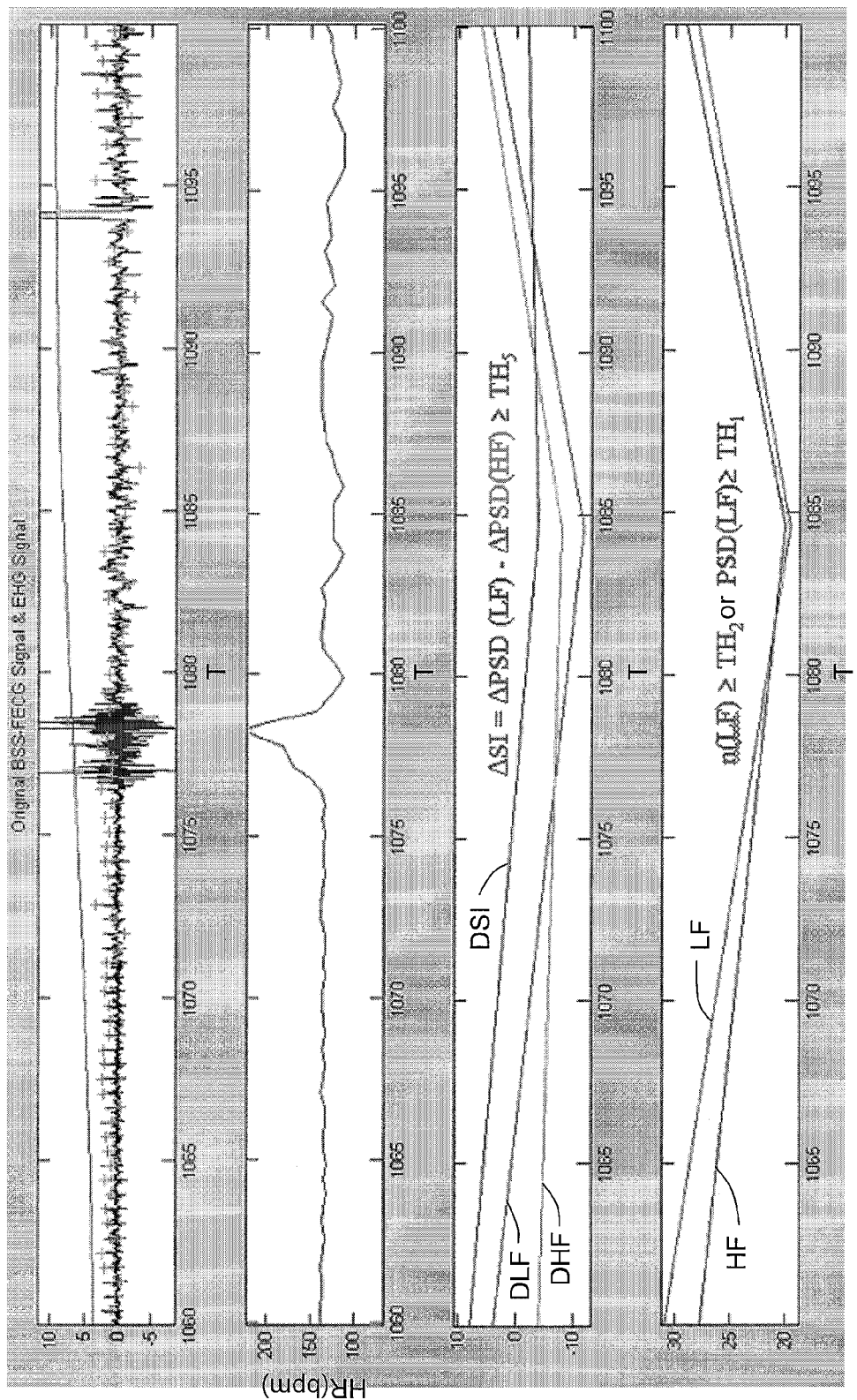
Figure 29:
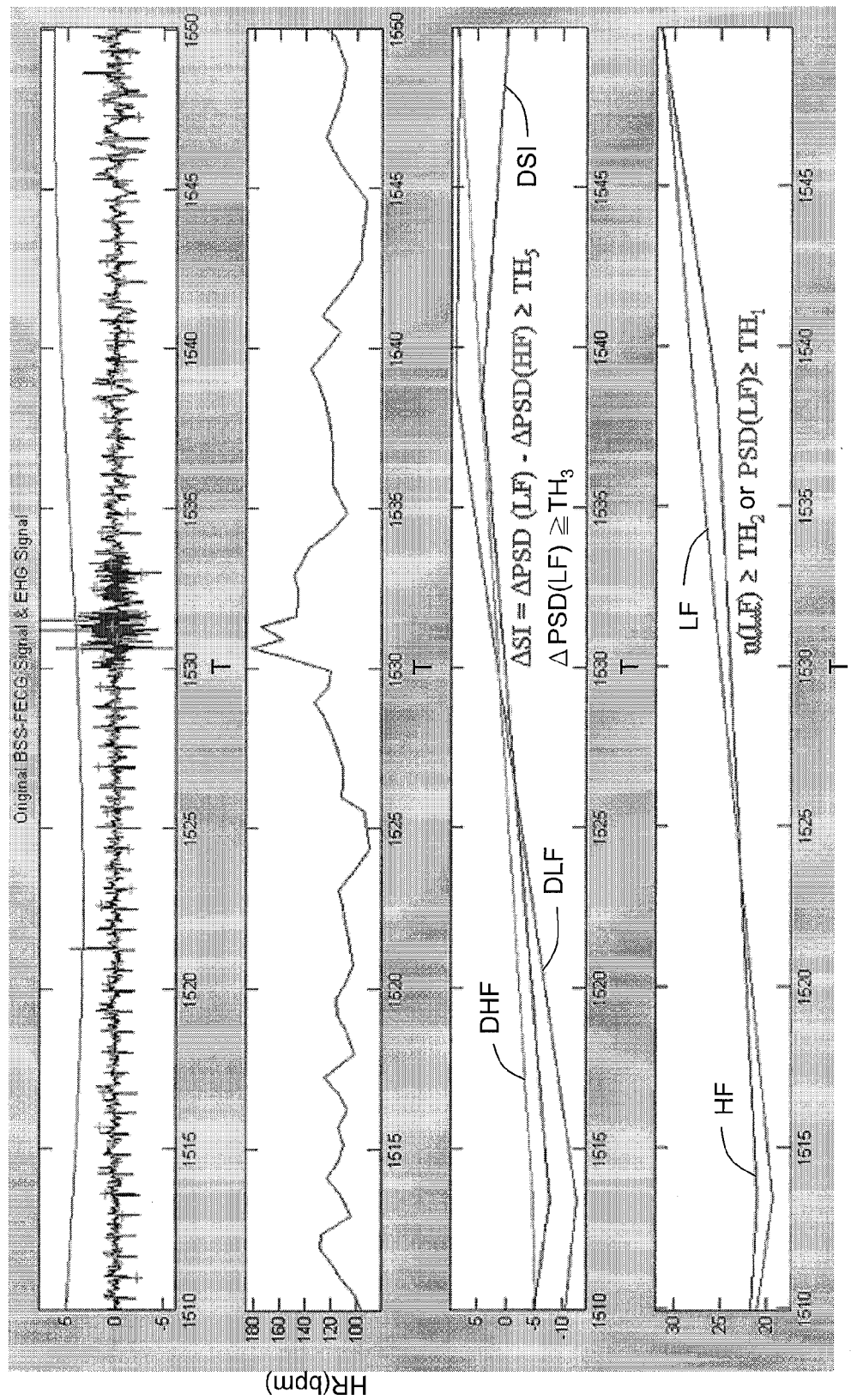
Figure 30:
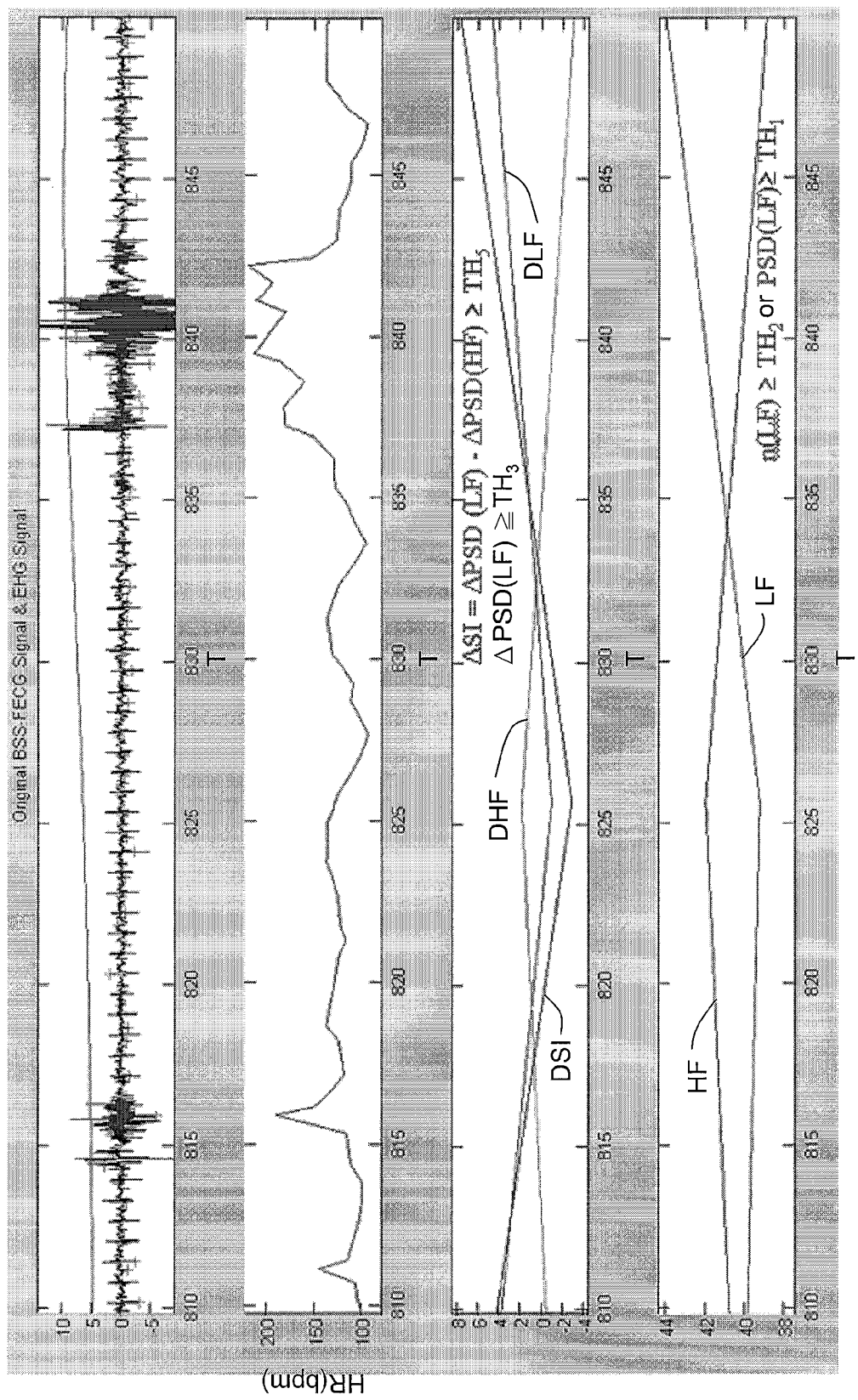
Figure 31:
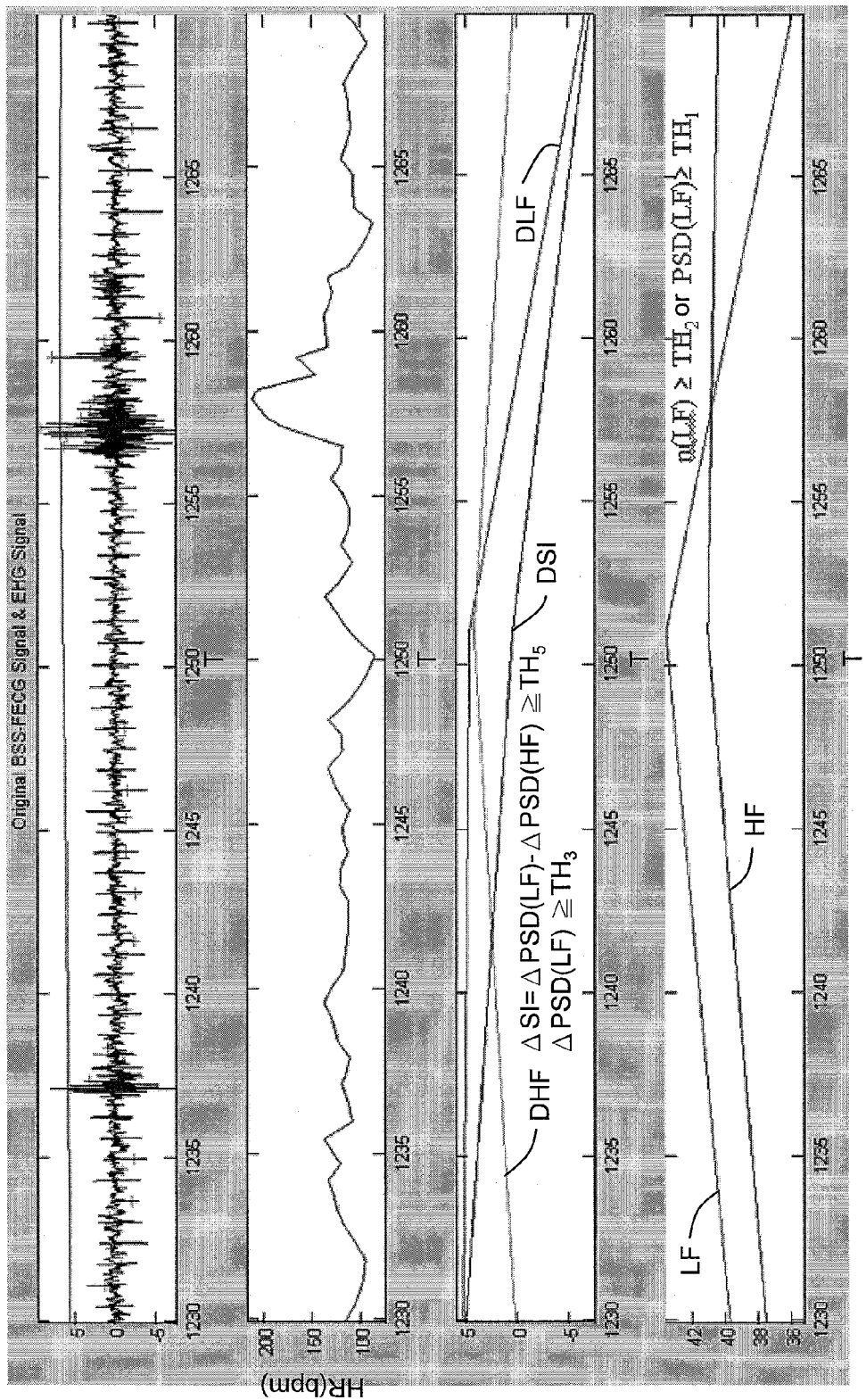
Figure 32:
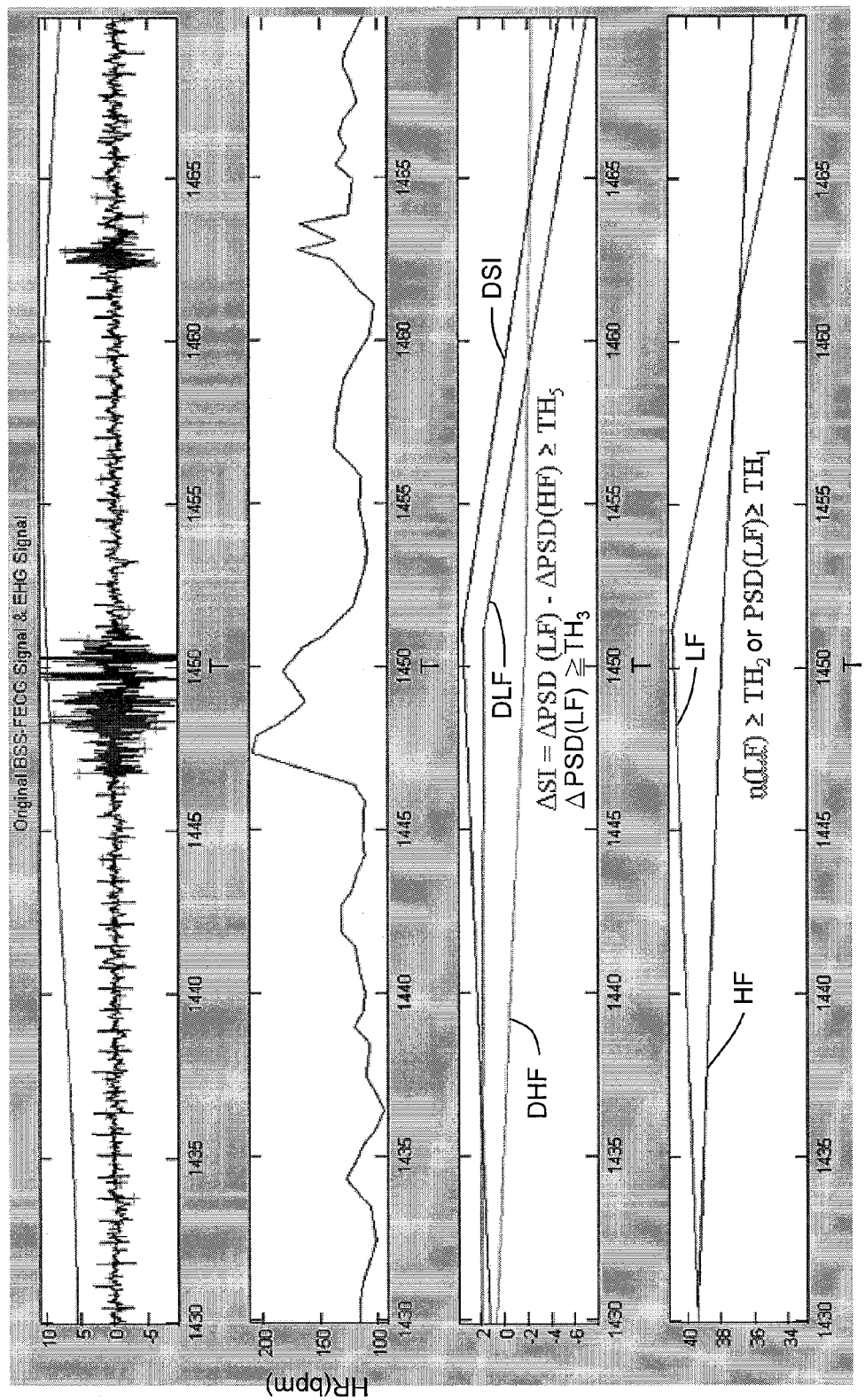
Figure 33:
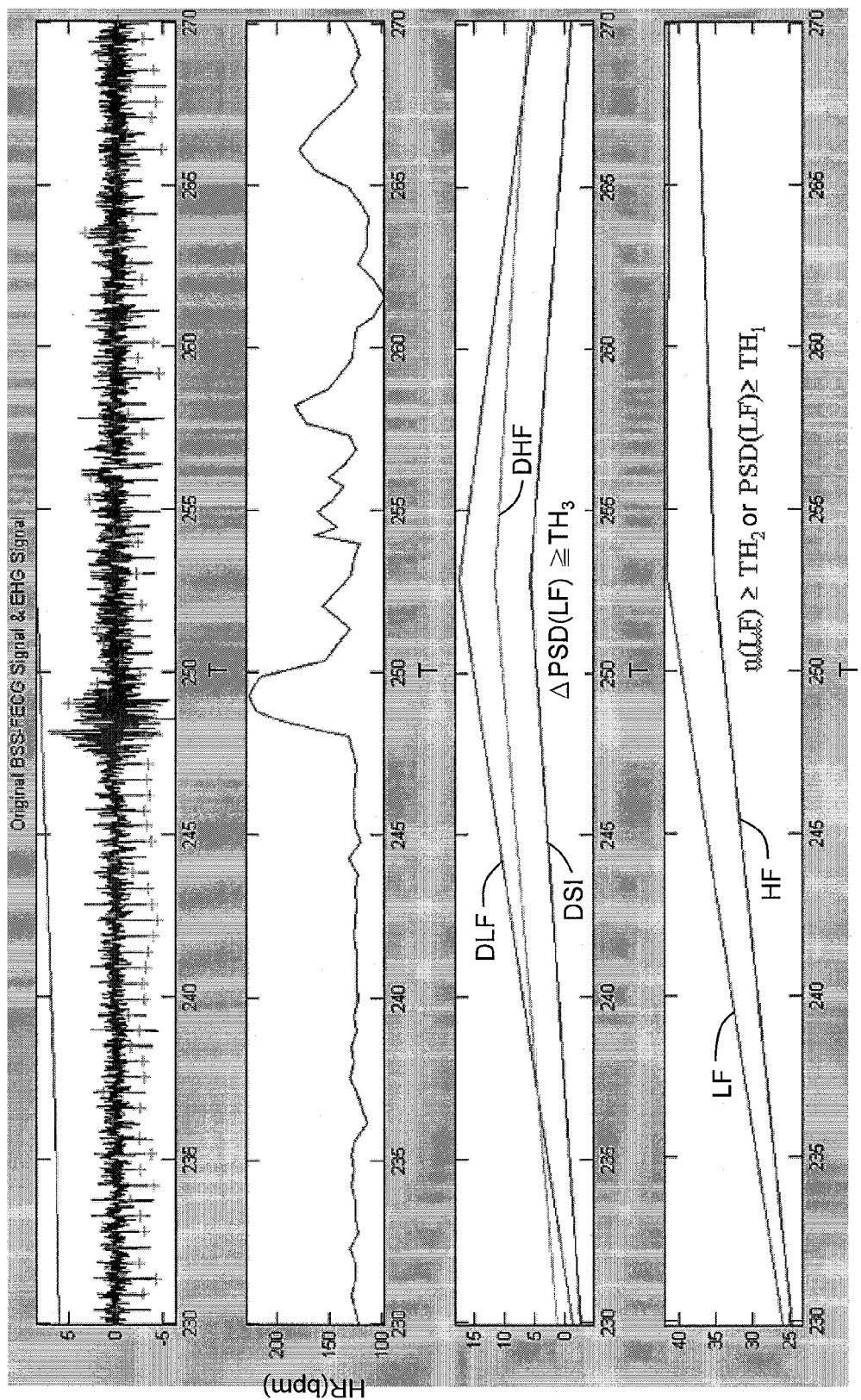
Figure 34:
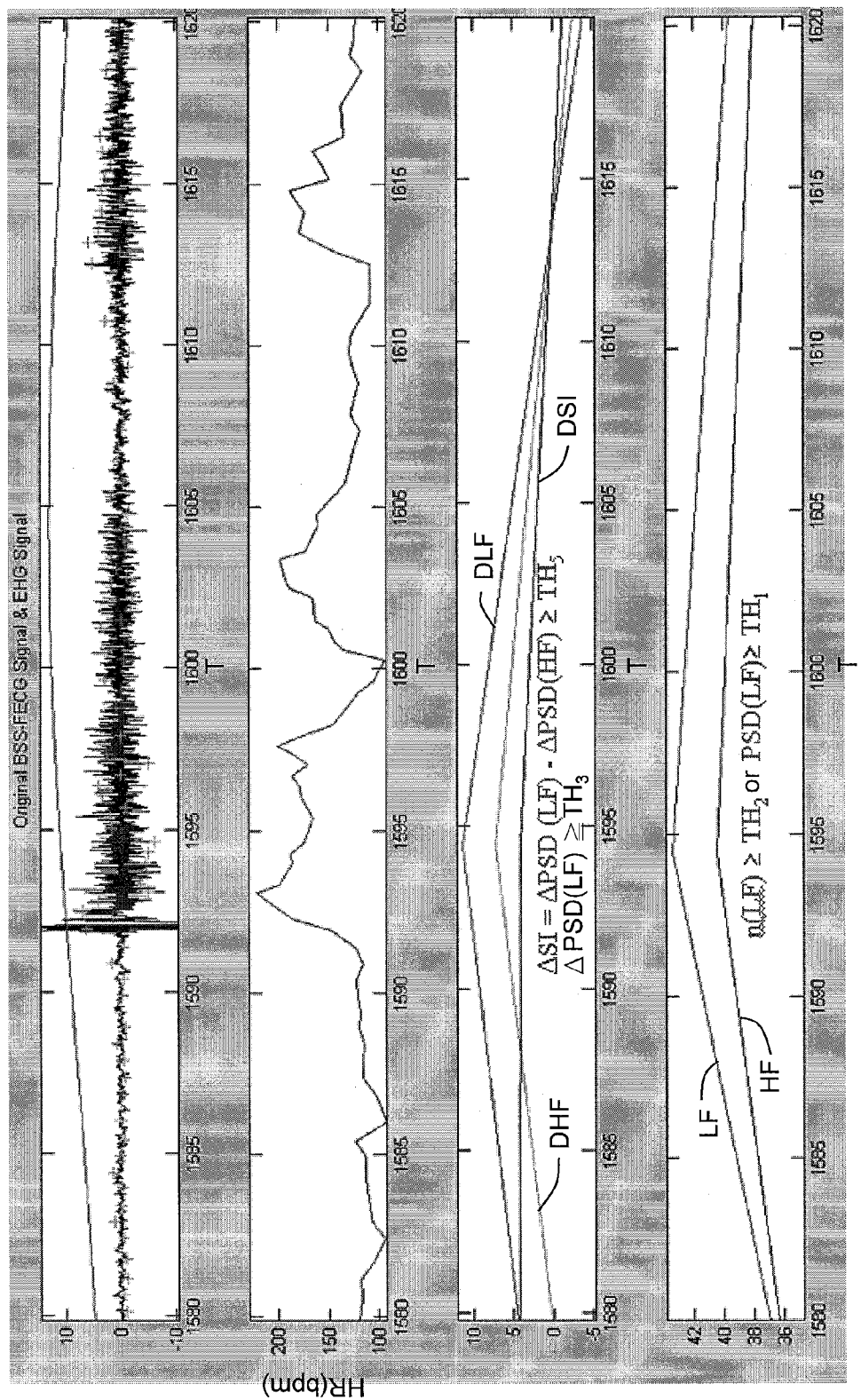
Figure 35:
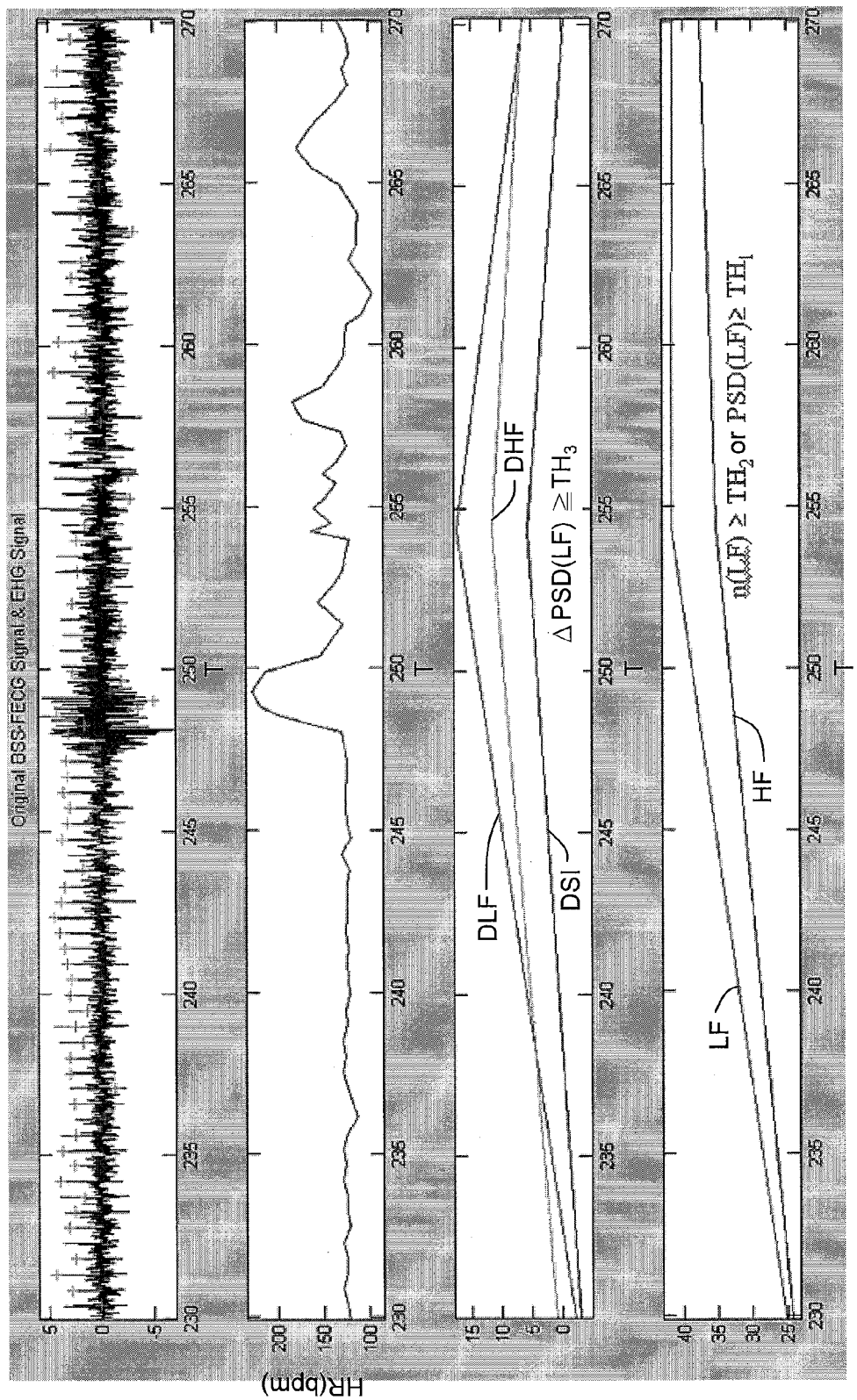
Figure 36:
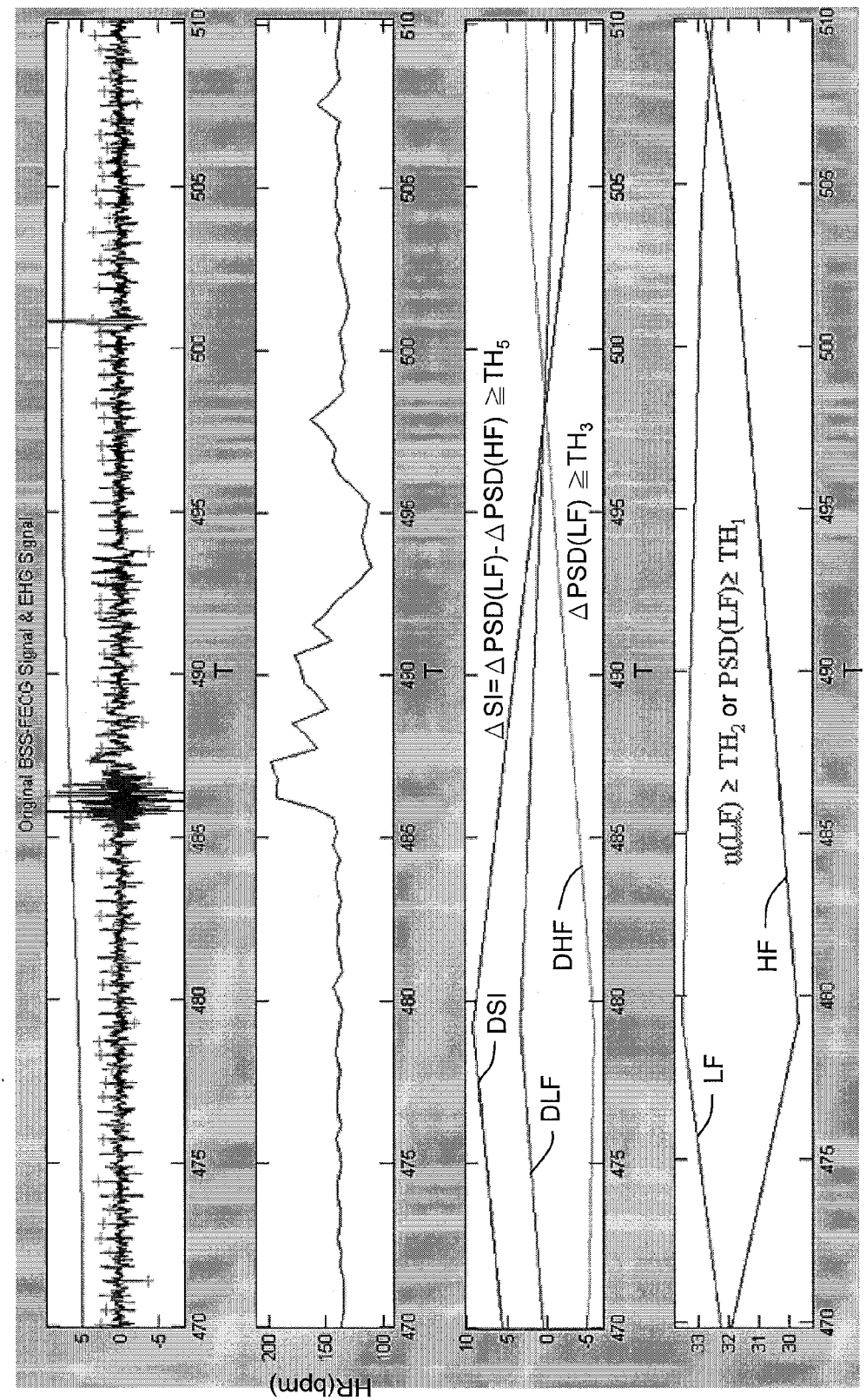
Figure 37:
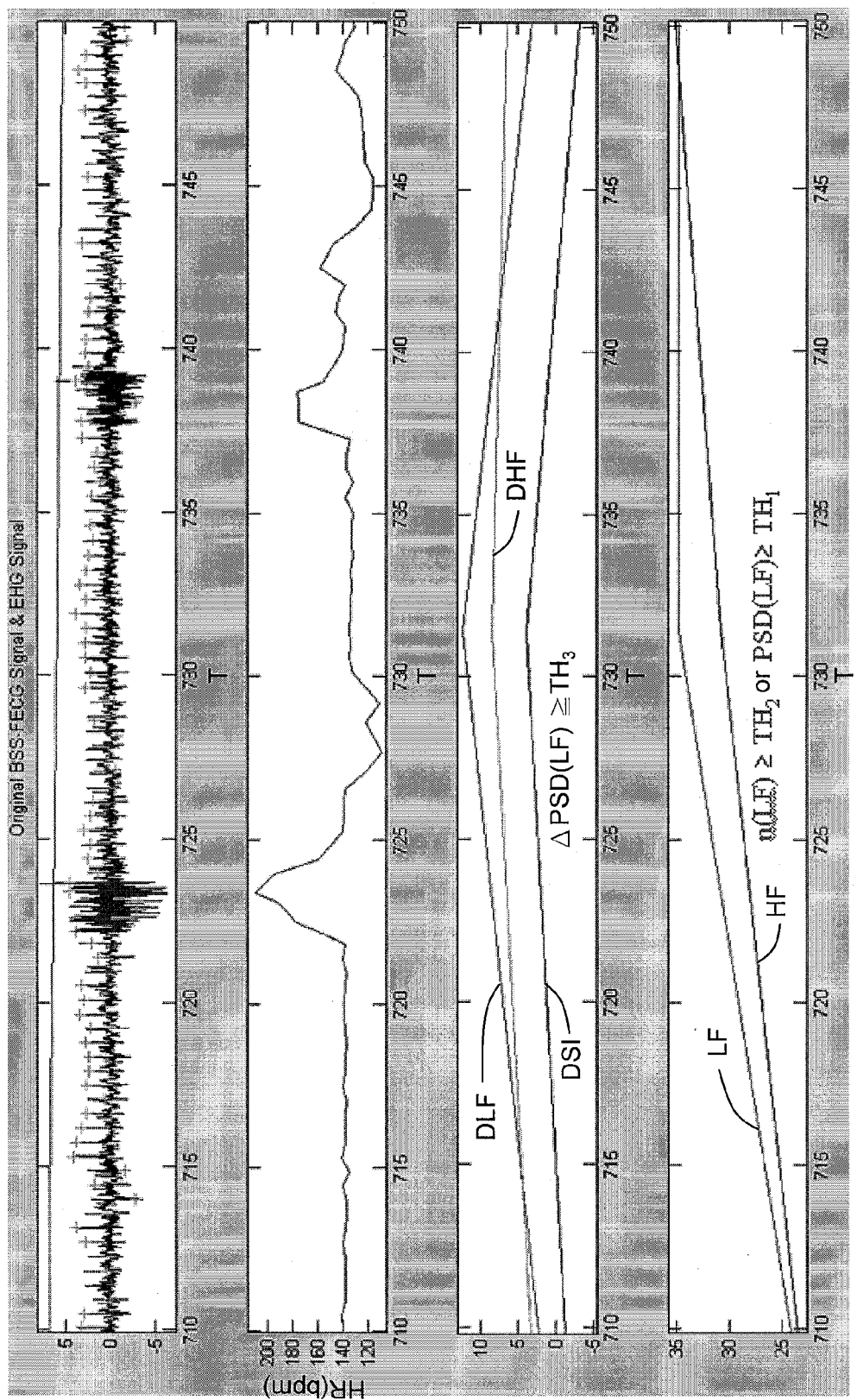
Figure 38:
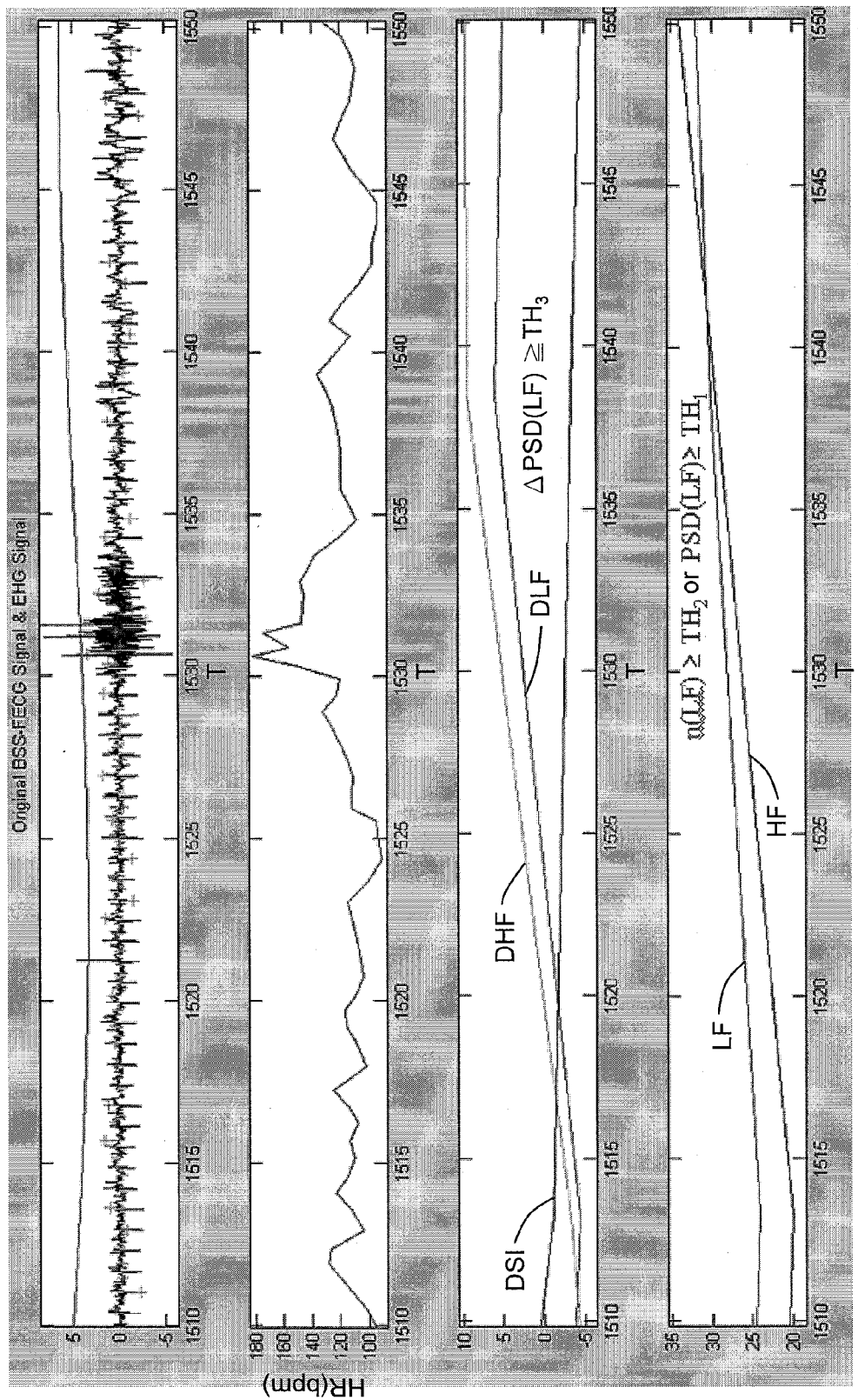
Figure 39:
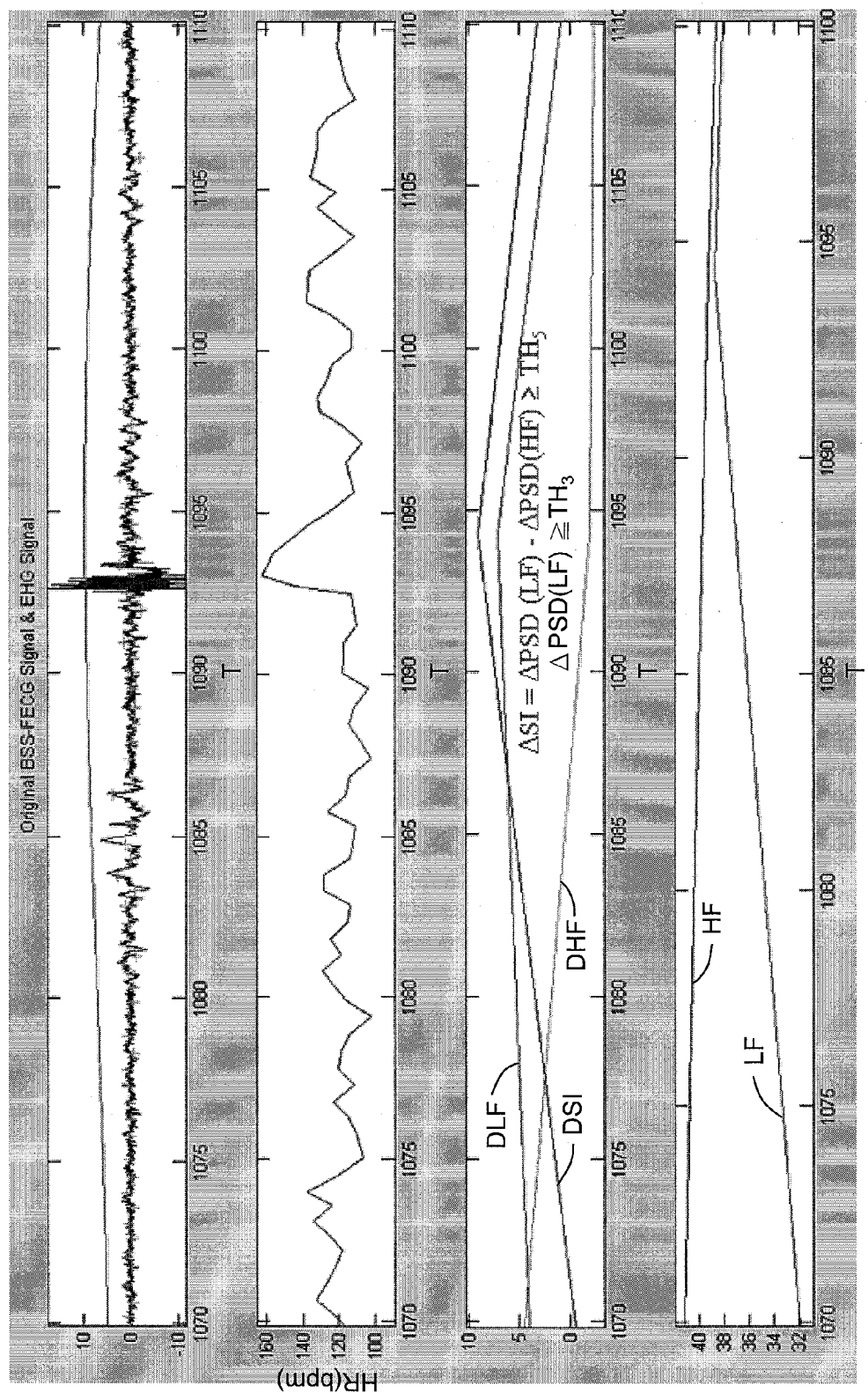
Figure 40:
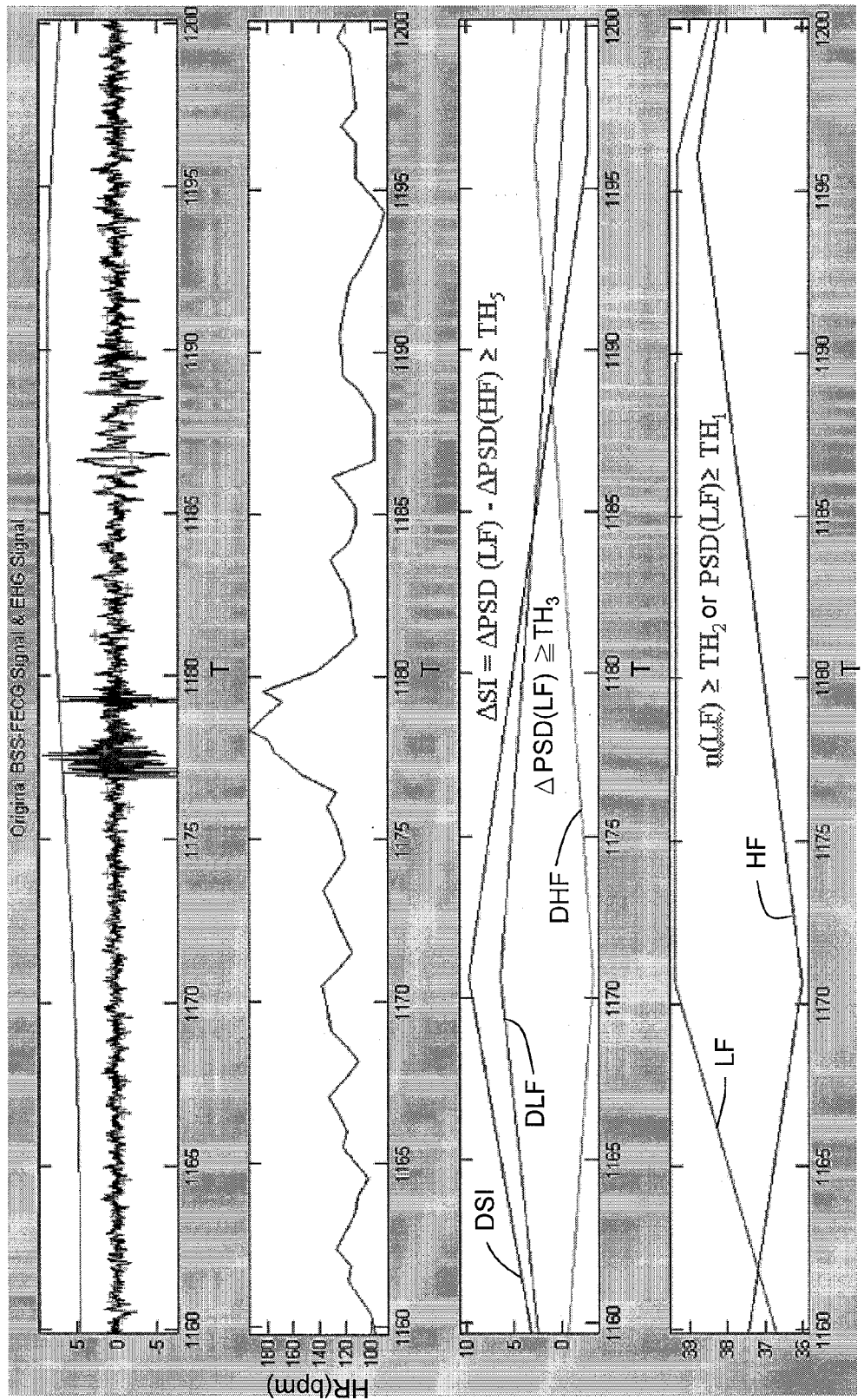
Figure 41:
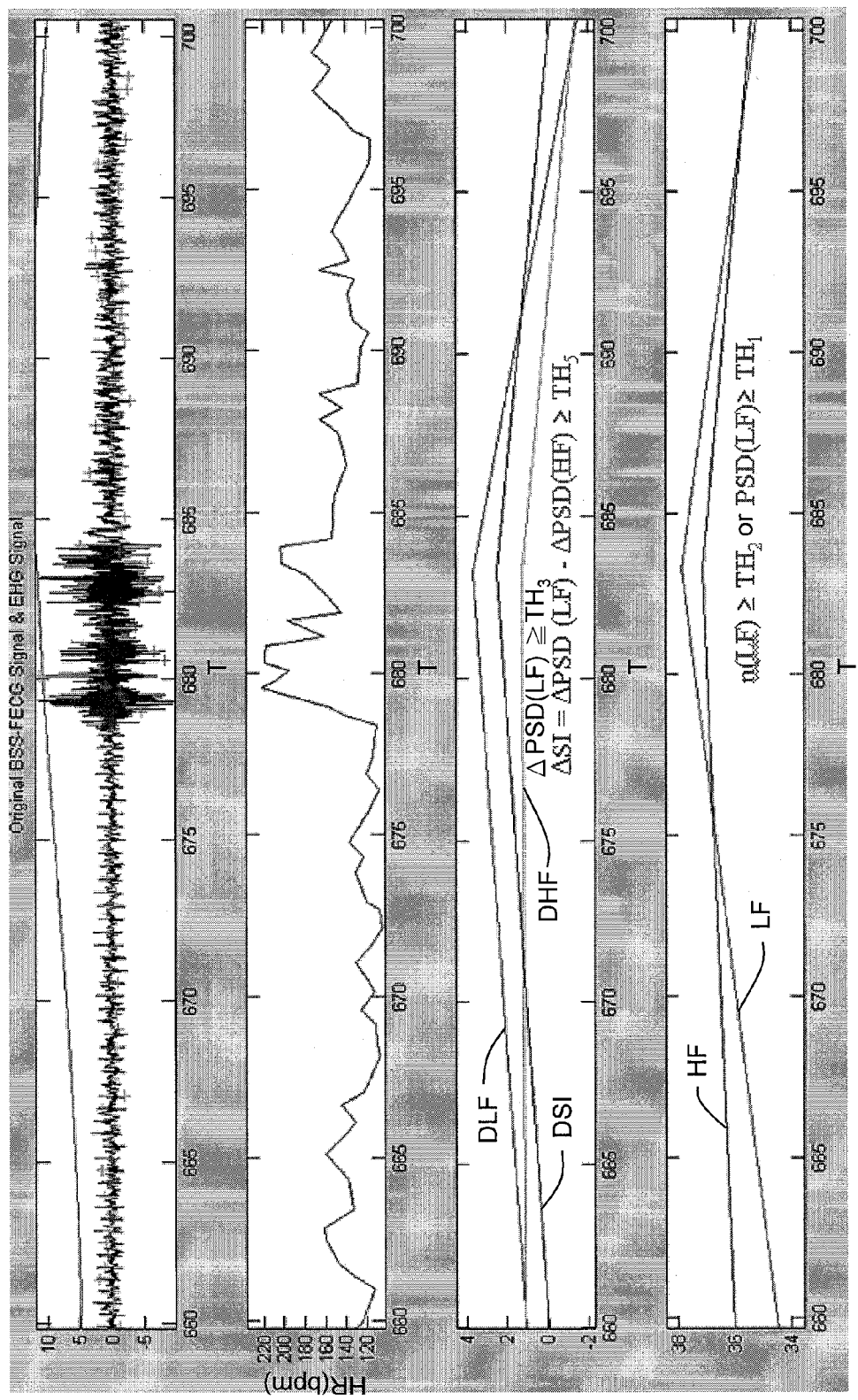
Figure 42:
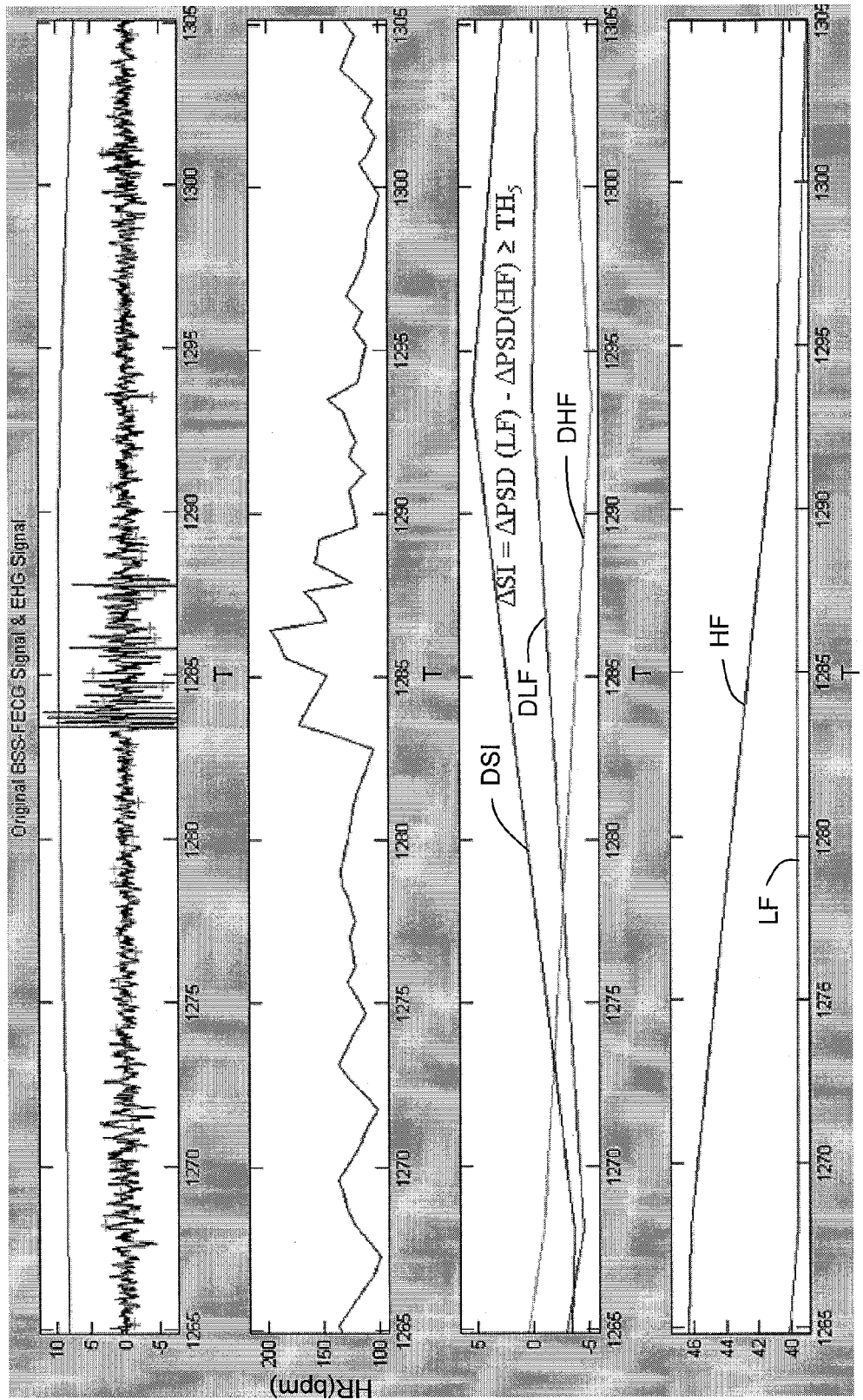
Figure 43:
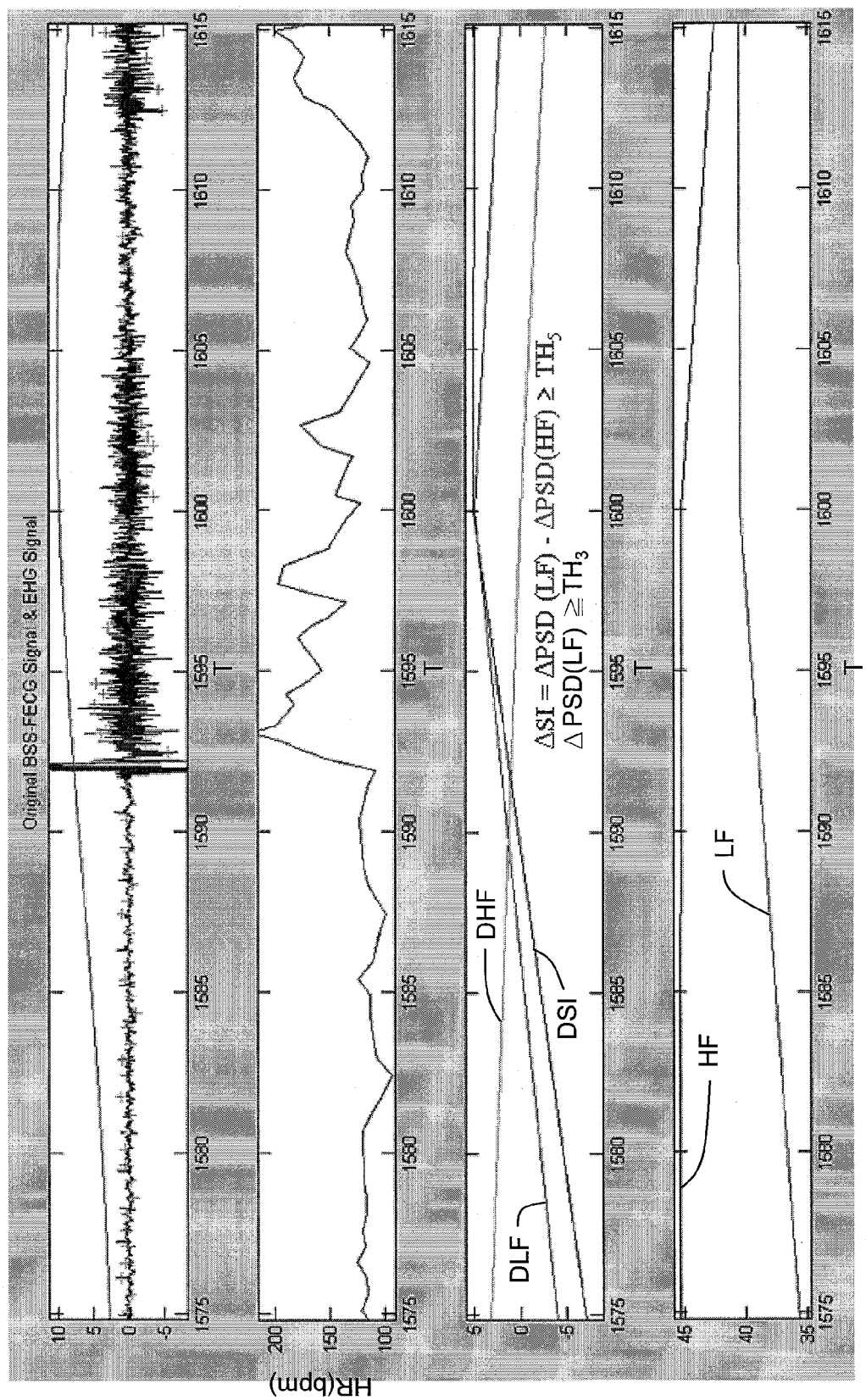

Referring to FIG. 23, the situations illustrated in FIG. 21 and FIG. 22 are combined so that the determination condition is set as that the sympathetic signal efference increases relatively if $\Delta SI = \Delta PSD(LF) - \Delta PSD(HF)$ increases for over the threshold (for example, $\Delta SI \geq TH_5 > 0$). FIGS. 24-43 illustrate the measurements of four signals according to embodiments of the present invention. Referring to FIG. 24-43, the abscissa indicates time in unit of seconds, and according to the time domain determination method, it is determined that the sympathetic nerve is active if the heart rate (HR) increase for over 15 bpm and lasts for at least 15 seconds.

The frequency domain determination method may include: PSD(HF) is a HF spectrum integral and which represents the intensity of a parasympathetic excitation signal, and PSD(LF) is a LF spectrum integral and which represents the intensity of a sympathetic and a partial parasympathetic excitation signal.

The activity of the sympathetic nerve can be determined through the method illustrated in FIGS. 20-23 as following:
A. it is sympathetic nerve dominant if PSD(LF) exceeds a threshold (for example, $PSD(LF) \geq TH_1$);
B. it is sympathetic nerve dominant if $\text{norm}(LF) = PSD(LF)/[PSD(LF) + PSD(HF)]$ exceeds a threshold (for example, $\text{norm}(LF) \geq TH_2$);
C. the sympathetic signal efference increases if PSD(HF) doesn't change while the PSD(LF) increases for over a threshold (for example, $\Delta PSD(LF) \geq TH_3 > 0$);
D. the parasympathetic signal efference decreases if PSD(LF) doesn't change while PSD(HF) decreases for over a threshold (for example, $0 > TH_4 \geq \Delta PSD(HF)$); and
E. the sympathetic signal efference relatively increases if $\Delta PSD(LF) - \Delta PSD(HF)$ increases for over a threshold (for example, $\Delta SI \geq TH_5 > 0$).

In FIGS. 24-43, bpm (beats per minute) refers the number of beats within each minute. A regular HF is an integral in the HF portion of the spectrum, and which reflects the parasympathetic nerve response. A regular LF is an integral in the LF portion of the spectrum, and which reflects the response of a sympathetic nerve and a partial parasympathetic nerve.

In other words, in the present invention, the activity of a sympathetic nerve can be precisely determined, and accordingly the accuracy in fetal movement detection is increased.

In the present invention, a plurality of (for example, at least 5) sensors is adopted to form at least three measuring leads. One of the sensors may be attached under the navel on the abdomen of the maternal body as a reference point, the sensor attached at the right side forms a measuring lead 1+, the sensor attached at the top side forms a measuring lead 2+, and the sensor attached at the left side forms a measuring lead 3+, so as to form three major measuring leads. In addition, other sensors may be further attached to form other measuring leads and to provide more assistant signals for separating mixed waves. The obtained sensing signals are pre-processed to filter out the noises and then output in two groups. The first group of physiological signals is brought into a mixed wave separation algorithm to obtain individual physiological signals, wherein the FECG signals are processed through an R-wave identification algorithm and a heart rate conversion method, so as to obtain a fetal heart rate timing diagram. The RRI of the FECG is processed through a short-timed Fourier transform to obtain a FECG time-frequency chart. The fetal heart rate timing diagram and the FECG time-frequency chart are used for identifying the activity of the sympathetic nerve.

Figure 3:
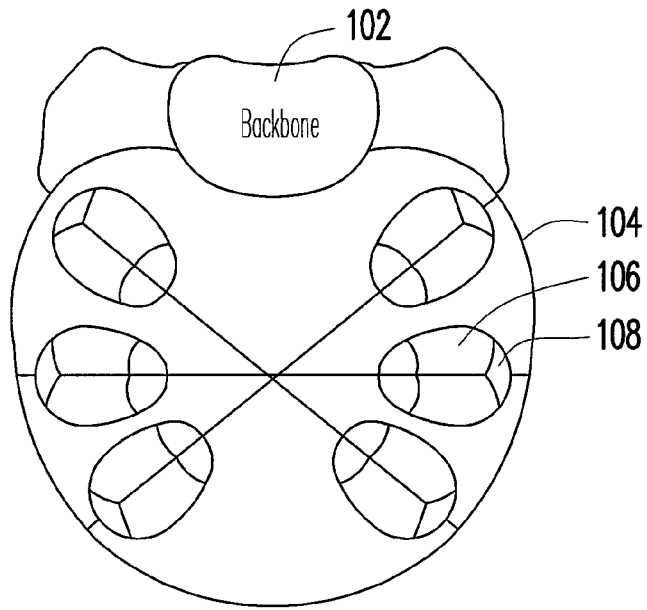
FIG. 3 is a cross-sectional view illustrating the directions of a fetal position with respect to a maternal body.
Figure 4:
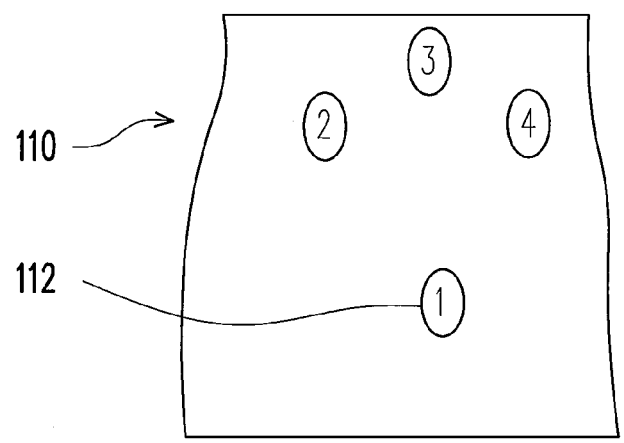
FIG. 4 illustrates a conventional technique of attaching physiological sensors on an abdomen.
Figure 5:
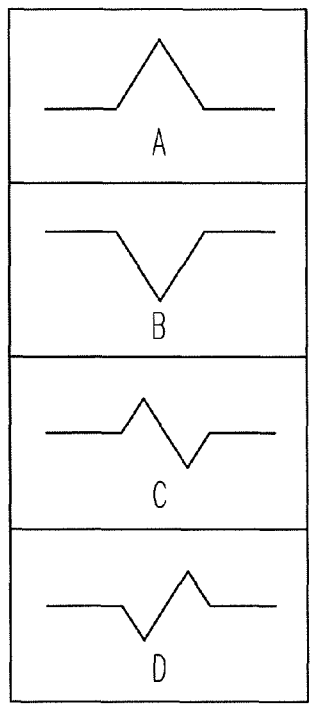
FIG. 5 illustrates four conventional electrocardiogram (ECG) categories.

The second group of physiological signals is mainly the physiological ECG signals measured through the three measuring leads and which are input into a digital filter. Besides reducing BD in the signals, ECGs and uterine contraction signals are separated out, and the uterine contraction signals in the three measuring leads are detected through the method illustrated in FIG. 3, so as to determine physiological uterine contraction and Braxton Hicks contraction. It is determined to be a physiological uterine contraction if signals are detected in all three measuring leads and last for at least 15 seconds. In addition, the current fetal position and the fetal movement are determined through the two fetal position identification methods provided by the present invention so as to find out the position-changing fetal movement. The variation of the EFCG/MECG in each of the measuring leads is detected with respect to, for example, shifting fetal movement. Moreover, a Braxton Hicks contraction is detected in the three measuring leads with respect to the limb fetal movement. Furthermore, an active fetal movement event is detected according to the activity of the sympathetic nerve.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A maternal uterine contraction and fetal movement monitoring apparatus, configured to monitor a maternal body and a fetus, the maternal uterine contraction and fetal movement monitoring apparatus comprising:
   a plurality of sensors, attached on an abdomen of the maternal body configured to provide at least three measuring leads;
   a signal pre-processor, configured to receive a plurality of sensing signals from the sensors, and configured to reduce noises in the sensing signals and amplify the sensing signals to output a plurality of characteristic sensing signals;
   a first signal post-processor, configured to receive the characteristic sensing signals from the signal pre-processor, and to filter noises out of the characteristic sensing signals to obtain a plurality of information of the maternal body and the fetus, wherein the information comprises a maternal electrocardiogram (MECG) signal, a maternal uterine electromyography (EMG) signal, and a FECG signal;

a first analysis unit, configured to calculate a fetal sympathetic nerve activity signal according to the information obtained by the first signal post-processor;

a second signal post-processor, configured to receive the characteristic sensing signals from the signal pre-processor and separate out a plurality of FECGs and a plurality of maternal uterine contraction signals corresponding to the measuring leads;

a second analysis unit, configured to receive signals output by the second signal post-processor, analyze the FECG and a MECG corresponding to each of the measuring leads to monitor an energy variation, and obtain a uterine contraction status signal according to the maternal uterine contraction signals; and a third analysis unit, configured to determine whether there is a fetal movement according to the uterine contraction status signal, the energy variation signals, and the fetal sympathetic nerve activity signal through a fetal movement identification technique, wherein the fetal sympathetic nerve activity signal increases an accuracy in detecting the fetal movement, wherein a fetal movement is determined if the FECGs corresponding to the measuring leads change and the fetal sympathetic nerve activity signal reflects a positive result.

2. The maternal uterine contraction and fetal movement monitoring apparatus according to claim 1 further comprising an event recording unit configured to record each transceiving event.

3. The maternal uterine contraction and fetal movement monitoring apparatus according to claim 1, wherein the sensors comprise at least five sensors, a first sensor is attached below a navel, a second sensor, a third sensor, and a fourth sensor for three measuring leads at a right position, a top position, and a left position, and a fifth sensor is attached elsewhere, wherein the first sensor and the fifth sensor provide assistant signals configured to cancel noises and separating mixed waves.

4. The maternal uterine contraction and fetal movement monitoring apparatus according to claim 1, wherein a uterine contraction is determined if the uterine contraction status signals are detected in all the measuring leads and last for a predetermined time.

5. The maternal uterine contraction and fetal movement monitoring apparatus according to claim 1, wherein the fetal sympathetic nerve activity signal reflects the positive result when a baseline of a fetal heart rate chart rises more than 15 bpm for over 15 seconds.

6. The maternal uterine contraction and fetal movement monitoring apparatus according to claim 1, wherein the fetal sympathetic nerve activity signal reflects the positive result when a nominal power of a low frequency section in a frequency spectrum between two consecutive R-wave peaks of the fetus exceeds a threshold.

7. A maternal uterine contraction and fetal movement monitoring method, for monitoring a maternal body and a fetus, the maternal uterine contraction and fetal movement monitoring method comprising:

attaching a plurality of sensors on an abdomen of the maternal body to provide at least three measuring leads;

receiving a plurality of sensing signals from the sensors, and reducing noises in the sensing signals and amplifying the sensing signals to output a plurality of characteristic sensing signals;

receiving the characteristic sensing signals, and filtering noises out of the characteristic sensing signals to obtain a plurality of information of the maternal body and the fetus, wherein the information comprises a MECG signal, a maternal uterine electromyography (EMG) signal, and a FECG signal;

calculating a fetal sympathetic nerve activity signal according to the information;

receiving the characteristic sensing signals from the signal pre-processor, and separating out a plurality of FECGs and a plurality of maternal uterine contraction signals corresponding to the measuring leads;

analyzing the FECGs to obtain the FECG and a MECG for each of the measuring leads, so as to determine whether the fetal position changes, and obtaining a uterine contraction status signal according to the maternal uterine contraction signals; and determining whether there is a fetal movement according to the uterine contraction status signal, the energy variation signals, and the fetal sympathetic nerve activity signal through a fetal movement identification technique, wherein the fetal sympathetic nerve activity signal increases an accuracy in detecting the fetal movement, wherein a fetal movement is determined when the electrocardiogram configuration of the FECGs corresponding to the measuring leads changes and the fetal sympathetic nerve activity signal reflects a positive result.

8. The maternal uterine contraction and fetal movement monitoring method according to claim 7, wherein a uterine contraction is determined if the uterine contraction status signals are detected in all the measuring leads and last for a predetermined time.

9. The maternal uterine contraction and fetal movement monitoring method according to claim 7, wherein the fetal sympathetic nerve activity signal reflects the positive result when a baseline of a fetal heart rate chart rises more than 15 bpm for over 15 seconds.

10. The maternal uterine contraction and fetal movement monitoring method according to claim 7, wherein the fetal sympathetic nerve activity signal reflects the positive result when a nominal power of a low frequency section in a frequency spectrum between two consecutive R-wave peaks of the fetus exceeds a threshold.

* * * * *